(12) United States Patent
Dannhardt et al.

(10) Patent No.: US 9,012,659 B2
(45) Date of Patent: Apr. 21, 2015

(54) 3-(INDOLYL)- OR 3-(AZAINDOLYL)-4-ARYLMALEIMIDE COMPOUNDS AND THEIR USE IN TUMOR TREATMENT

(75) Inventors: Gerd Dannhardt, Mainz (DE);
Jan-Peter Kramb, Mainz (DE);
Stanislav Plutizki, Mainz (DE)

(73) Assignee: Johannes Gutenberg—Universitat Mainz, Mainz (DE)

( * ) Notice: Subject to any disclaimer, the term of this patent is extended or adjusted under 35 U.S.C. 154(b) by 162 days.

(21) Appl. No.: 13/517,004

(22) PCT Filed: Dec. 10, 2010

(86) PCT No.: PCT/EP2010/069352
§ 371 (c)(1),
(2), (4) Date: Feb. 5, 2013

(87) PCT Pub. No.: WO2011/073092
PCT Pub. Date: Jun. 23, 2011

(65) Prior Publication Data
US 2013/0131060 A1 May 23, 2013

(30) Foreign Application Priority Data
Dec. 18, 2009 (EP) .................................... 09179986

(51) Int. Cl.
| | |
|---|---|
| A61K 31/4375 | (2006.01) |
| C07D 403/10 | (2006.01) |
| C07D 471/04 | (2006.01) |
| A61K 31/5377 | (2006.01) |
| C07D 403/04 | (2006.01) |
| A61K 31/404 | (2006.01) |
| A61K 31/437 | (2006.01) |
| A61K 31/454 | (2006.01) |
| A61K 31/4745 | (2006.01) |
| A61K 31/496 | (2006.01) |
| A61K 45/06 | (2006.01) |

(52) U.S. Cl.
CPC .......... *A61K 31/5377* (2013.01); *C07D 403/04* (2013.01); *C07D 471/04* (2013.01); *A61K 31/404* (2013.01); *A61K 31/437* (2013.01); *A61K 31/454* (2013.01); *A61K 31/4745* (2013.01); *A61K 31/496* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,057,614 A | * | 10/1991 | Davis et al. | 548/466 |
| 5,260,451 A | * | 11/1993 | Dannhardt et al. | 548/453 |
| 5,721,245 A | | 2/1998 | Davis et al. | |
| 5,959,261 A | * | 9/1999 | Abelson | 181/131 |
| 7,125,878 B2 | * | 10/2006 | Zhang et al. | 514/255.05 |
| 7,232,906 B2 | * | 6/2007 | Zhang et al. | 544/333 |
| 7,488,826 B2 | * | 2/2009 | Zhang et al. | 546/113 |
| 7,524,858 B2 | * | 4/2009 | Zhang et al. | 514/300 |
| 7,705,015 B2 | * | 4/2010 | Zhang et al. | 514/300 |
| 7,781,450 B2 | * | 8/2010 | Zhang et al. | 514/300 |
| 7,786,135 B2 | * | 8/2010 | Zhang et al. | 514/300 |
| 8,008,320 B2 | * | 8/2011 | Dannhardt et al. | 514/300 |
| 8,841,319 B2 | | 9/2014 | Dannhardt | |
| 2004/0006095 A1 | * | 1/2004 | Zhang et al. | 514/256 |
| 2004/0054180 A1 | * | 3/2004 | Zhang et al. | 544/333 |
| 2004/0192718 A1 | * | 9/2004 | Zhang et al. | 514/300 |
| 2006/0205762 A1 | * | 9/2006 | Zhang et al. | 514/300 |
| 2006/0205763 A1 | * | 9/2006 | Zhang et al. | 514/300 |
| 2009/0093515 A1 | * | 4/2009 | Zhang et al. | 514/300 |
| 2009/0093634 A1 | * | 4/2009 | Zhang et al. | 546/113 |
| 2009/0176806 A1 | * | 7/2009 | Zhang et al. | 514/255.05 |
| 2009/0181982 A1 | * | 7/2009 | Zhang et al. | 514/255.05 |
| 2009/0306124 A1 | * | 12/2009 | Dannhardt et al. | 514/300 |
| 2013/0029986 A1 | | 1/2013 | Dannhardt | |
| 2013/0345281 A1 | | 12/2013 | Dannhardt | |

FOREIGN PATENT DOCUMENTS

| | | |
|---|---|---|
| EP | 0328026 A1 | 8/1989 |
| EP | 0384349 A1 | 8/1990 |
| EP | 0540956 A1 | 5/1993 |
| EP | 1224932 A1 | 7/2002 |
| WO | WO 91/13071 A1 | 9/1991 |

(Continued)

OTHER PUBLICATIONS

Cash et al., "Excited state tautomerization of azaindole", *Org. Biomol. Chem.*, 3, 3701-3706 (2005).

(Continued)

*Primary Examiner* — Nyeemah A Grazier
(74) *Attorney, Agent, or Firm* — Viksnins Harris & Padys PLLP

(57) ABSTRACT

The present invention relates to a compound of formula (I) wherein $R^1$, $R^2$ and $R^3$ are as defined in the description and the physiologically acceptable salts thereof as well as the physiologically acceptable solvates of the compounds of formula I and of the salts thereof. The compounds of formula I are suitable for treating tumors.

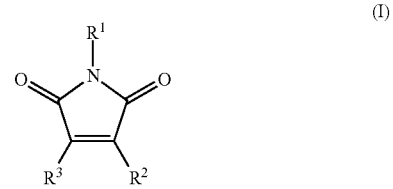

(I)

10 Claims, No Drawings

(56) References Cited

FOREIGN PATENT DOCUMENTS

| WO | WO 95/07910 A1 | 3/1995 |
|---|---|---|
| WO | WO 97/34890 A1 | 9/1997 |
| WO | WO 00/21927 A2 | 4/2000 |
| WO | WO 00/38675 A1 | 7/2000 |
| WO | WO 02/10158 A2 | 2/2002 |
| WO | WO 02/38561 A1 | 5/2002 |
| WO | WO 03/057202 A1 | 7/2003 |
| WO | WO 03/095452 A1 | 11/2003 |
| WO | WO 03/103663 A2 | 12/2003 |
| WO | WO 2006/061212 A1 | 6/2006 |
| WO | WO 2009/010542 A1 | 1/2009 |

OTHER PUBLICATIONS

Faul et al., "A New One Step Synthesis of Maleimides by Condensation of Glyoxylate Esters with Acetamides", *Tetrahedron Letters*, 40, 1109-1112 (1999).
Hands et al., "A Convenient Method for the Preparation of 5-, 6- and 7-Azaindoles and Their Derivatives", *Synthesis* 7, 877-882 (1996).
Mahadevan et al., "Synthesis of Pyrrolopyridines (Azaindoles)", *Heterocyclic Chem.* 29, 359-367 (1992).
Okauchi et al., "A General Method for Acylation of Indoles at the 3-Position with Acyl Chlorides in the Presence of Dialkylaluminum Chloride", *Organic Letters*, vol. 2, No. 10, 1485-1487 (2000).
Patent Cooperation Treaty, International Search Report and Written Opinion for PCT/EP2010/069352, 9 pages, Mar. 9, 2011.
Peifer et al., "Design, Synthesis, and Biological Evaluation of 3,4-Diarylmaleimides as Angiogenesis Inhibitors", *J. Med. Chem.*, 49, 1271-1281 (2006).
Peifer et al., "Profile and Molecular Modeling of 3-(Indole-3-yl)-4-(3,4,5-trimethoxyphenyl)-1*H*-pyrrole-2,5-dione (1) as a Highly Selective VEGF-R2/3 Inhibitor", *J. Med. Chem.*, 49, 7549-7553 (2006).
Tholander et al., "Syntheses of 6,12-Disubstituted 5,11-Dihydroindolo[3,2-*b*]carbazoles, Including 5,11-Dihydroindolo[3,2-*b*]carbozole-6,12-dicarbaldehyde, an Extremely Efficient Ligand for the TCDD (Ah) Receptor", *Tetrahedron 55*, 12577-12694 (1999).
Zhang et al., "A General Method for the Preparation of 4-and 6-Azaindoles", *J. Org. Chem.*, 67, 2345-2347 (2002).
Zhang et al., "An Effective Procedure for the Acylation of Azaindoles at C-3", *J. Org. Chem.*, 67, 6226-6227 (2002).
Zhang et al., "3-(7-Azaindolyl)-4-arylmaleimides as potent, selective inhibitors of glycogen synthase kinase-3", *Bioorganic & Medicinal Chemistry Letters* 14, 3245-3250 (2004).

* cited by examiner

3-(INDOLYL)- OR 3-(AZAINDOLYL)-4-ARYLMALEIMIDE COMPOUNDS AND THEIR USE IN TUMOR TREATMENT

RELATED APPLICATIONS

This application is a U.S. 371 application of PCT/EP2010/069352, which was filed on 10 Dec. 2010, and claims the benefit of priority of European Application Serial No. 09179986.6, which was filed on 18 Dec. 2009.

The present invention relates to 3-(indolyl)- or 3-(azaindolyl)-4-arylmaleimide compounds, pharmaceutical compositions containing them and their use in tumor treatment.

Angiogenesis is a morphogenetic process which relates to the formation of new blood vessels from the endothelial cells of already existing capillary vessels. A number of pathological events in humans have been found to be associated with angiogenesis. Angiogenetic processes are pathologically responsible inter alia in rheumatoid arthritis, psoriasis, ischemia and malignant diseases. Angiogenesis plays an important role in genesis, growth and progression of tumors. Once tumors have reached a size of about 3 mm$^3$, their growth is completely dependent on this process. In general, tumors with a high expression of angiogenic factors, e.g. VEGF, bFGF, matrix metalloproteinases and serine proteases, and low levels of inhibitors of angiogenesis, e.g. thrombospondin and inhibitors of metalloproteinases, have a higher microvessel density, are locally more advanced, have a more aggressive behavior, and metastasize more frequently than tumors without this angiogenic phenotype.

Therefore, angiogenesis inhibitors are contemplated as potential therapeutic agents in the treatment of solid tumors for which no effective therapies are known so far, such as bronchial carcinoma, mamma carcinoma, prostate carcinoma, glioblastoma, Karposi sarcoma, melanoma, lymphoma and multiple myeloma.

Recently, it has been recognized that tumor growth and metastasis is highly associated with the overexpression of protein kinases (PK), which trigger intracellular signal transduction by phosphorylating tyrosine, threonine and serine residues in key proteins, therefore regulating cell growth, apoptosis resistance and survival. Targeting receptor tyrosine kinases proved to be an effective strategy in cancer treatment.

Several small molecule inhibitors of protein kinases (Imatinib, Gefitinib, Erlotinib, Sorafenib, and Sunitinib), which are currently under investigation in laboratory and clinical developmeat, showed promising efficacy and acceptable toxicity. Despite these first achievements, many tumors are still treatment resistant.

WO 02/38561 discloses kinase inhibitors of the formula

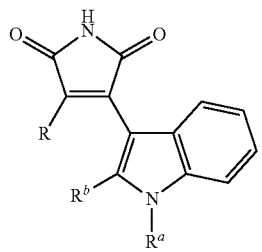

wherein R is an aryl radical such as a hydroxy substituted phenyl group.

Compounds of similar structure and having a comparable effect or other pharmacological activity are disclosed in EP 328 026 A, WO 02/10158, WO 03/057202, WO 03/095452, WO 03/103663, WO 95/07910, WO 00/38675, WO 97/34890, WO 91/13071, EP 384 349 A, EP 540 956, EP 1 224 932 A, WO 00/021927, and Bioorganic & Medicinal Chemistry Letters 14 (2004), 3245-3250.

WO 2006/061212 discloses compounds of formula I:

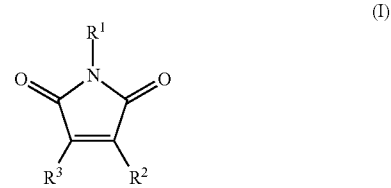

wherein
$R^1$ is H, $C_1$-$C_6$-alkyl, phenyl-$C_1$-$C_4$-alkyl or phenyl;
$R^2$ is a phenyl group which is substituted with 2 or 3 $C_1$-$C_6$-alkoxy groups, and
$R^3$ is indolyl or azaindolyl which may carry one or two substituents independently selected from $C_1$-$C_6$-alkyl, $C_1$-$C_6$-alkoxy, phenyl, OH, halogen, $NH_2$, $C_1$-$C_6$-alkylamino, di-$C_1$-$C_6$-alkylamino, heteroaryl with 5 or 6 ring atoms containing 1 or 2 heteroatoms which are independently selected from O, N, and S and heterocyclyl with 5 or 6 ring atoms containing 1 or 2 heteroatoms which are independently selected from O, N, and S and the physiologically acceptable salts thereof as well as the solvates of the compounds of formula I and of the salts thereof. The compounds are useful as angiogenesis inhibitors. J. Med. Chem. 2006, 49, 1271-1281 and J. Med. Chem. 2006, 49, 7549-7553 are concerned with the design, synthesis and evaluation of 3,4-diarylmaleimides as angiogenesis inhibitors.

The present invention relates to compounds of formula I:

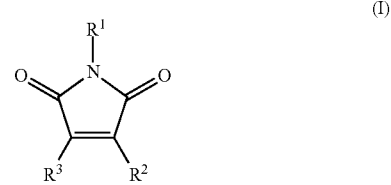

wherein
$R^1$ is H, $C_1$-$C_6$-alkyl, phenyl-$C_1$-$C_4$-alkyl or phenyl;
$R^2$ is a phenyl group which is substituted with 3 $C_1$-$C_6$-alkoxy groups, and
$R^3$ is selected from:

a)

b)
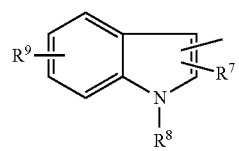

-continued c)
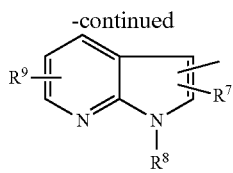

d)
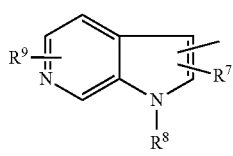

e)
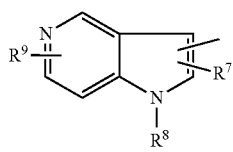

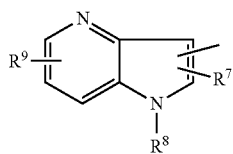

wherein $R^7$ is H or $C_1$-$C_6$-alkyl,
$R^8$ is $C_1$-$C_6$-alkyl-$R^{10}$ and $R^{10}$ is selected from
a) amino,
b) $C_1$-$C_6$-alkylamino,
c) di-$C_1$-$C_6$-alkylamino,
d) hydroxy,
e) $C_1$-$C_6$-alkoxy,
f) saturated heterocyclyl with 5 or 6 ring atoms containing a nitrogen heteroatom and optionally 1 or 2 additional heteroatoms which are independently selected from O, N and S, wherein the heterocyclyl is attached to the $C_1$-$C_6$-alkyl group via the nitrogen atom and may carry one, two, three or four $C_1$-$C_6$-alkyl substituents;
g) phenoxy,
h) benzyloxy,
i) $R^{11}CONR^{12}$—,
j) $NR^{12}R^{12}CO$—,
k) $C_1$-$C_6$-alkyl-NHCONH—,
l) $C_1$-$C_6$-alkyl-NHCOO—,
m) $C_1$-$C_6$-alkyl-OCONH—,
n) $R^{12}$—$OSO_2O$—,
o) $R^{11}SO_2O$—,
p) $R^{12}$—$OSO_2$—,
q) $R^{11}SO_2$—,
r) $(R^{12}O)_2P(O)O$—,
s) $(R^{12}O)_2P(O)$—, and
t) $(R^{12}O)R_{11}P(O)O$—;
$R^9$ is H, $C_1$-$C_6$-alkyl, $C_1$-$C_6$-alkoxy, OH, or halogen;
$R^{11}$ is $C_1$-$C_6$-alkyl;
$R^{12}$ is H or $C_1$-$C_6$-alkyl;
and the physiologically acceptable salts thereof as well as the solvates of the compounds of formula I and of the salts thereof.

The term "alkyl", "alkoxy", "alkylamino", "alkylene" etc. includes linear or branched alkyl or alkylene groups having 1 to 6 and preferably 1 to 4 carbon atoms. Examples for alkyl groups are methyl, ethyl, n-propyl, i-propyl, n-butyl, sec-butyl, iso-butyl, t-butyl, n-pentyl or n-hexyl. Examples for alkoxy groups are methoxy, ethoxy, n-propoxy, isopropoxy, n-butoxy. Examples for alkylene groups are methylene, ethylene, n-propylene, isopropylene, n-butylene, isobutylene etc.

Halogen means F, Cl, Br and I, preferably F and Cl.

Examples for heterocyclyl are pyrrolidinyl, imidazolidinyl, piperidinyl, morpholinyl, thiomorpholinyl and piperazinyl. In a particular embodiment heterocyclyl is piperidinyl, morpholinyl and piperazinyl. If heterocyclyl is substituted, the substituent may be at a carbon atom or at the additional nitrogen heteroatom. Examples for substituted heterocyclyl are 4-methylpiperazinyl or 2,2,6,6-tetramethylpiperidine.

Physiologically acceptable salts of the compounds of formula I include acid addition salts with inorganic acids, such as hydrochloric acid, sulfuric acid, or phosphoric acid, or with organic acids, in particular carboxylic acids, such as acetic acid, tartaric acid, lactic acid, citric acid, maleic acid, amygdalic acid, ascorbic acid, fumaric acid, gluconic acid or sulfonic acids, such as methane sulfonic acid, benzene sulfonic acid and toluene sulfonic acid.

Physiologically acceptable salts of the compounds of formula I include also base addition salts with inorganic bases, such as alkali metal hydroxides, like sodium or potassium hydroxyide, alkaline earth metal hydroxides, like magnesium or calcium hydroxide; ammonium salts, or salts with organic bases such as tetramethylammonium hydroxide, triethylamine, tri(hydroxyethyl)amine, lysine, arginine or glutamic acid.

Physiologically acceptable solvates are in particular hydrates.

An embodiment of the present invention includes compounds of formula (I) wherein $R^2$ is a group having the formula

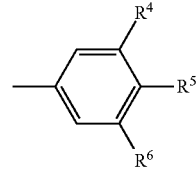

wherein $R^4$, $R^5$ and $R^6$ are $C_1$-$C_6$-alkoxy.

The indolyl or azaindolyl group, for example groups (a) to (e) are preferably attached to the maleimide group via the 3-position of the indolyl or azaindolyl group.

According to one embodiment, the present invention relates to the compounds of formula (Ia):

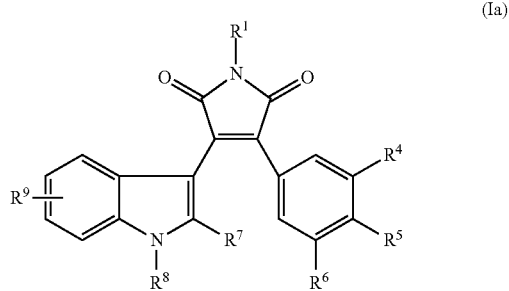

(Ia)

wherein $R^1$, and $R^4$ to $R^9$ have the meanings given above.

According to a further embodiment, the present invention relates to the compounds of formula (Ib):

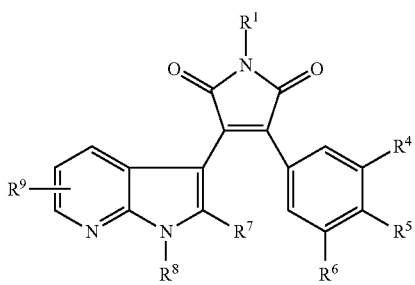

(Ib)

wherein $R^1$, and $R^4$ to $R^9$ are as defined above.

According to a further embodiment, the present invention relates to the compounds of formula (Ic):

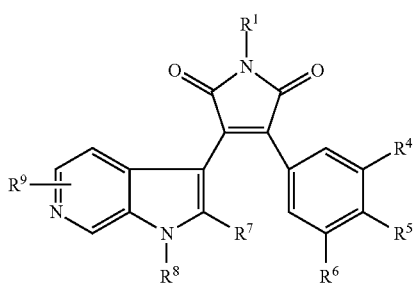

(Ic)

wherein $R^1$, and $R^4$ to $R^9$ are as defined above.

According to a further embodiment, the present invention relates to the compounds of formula (Id):

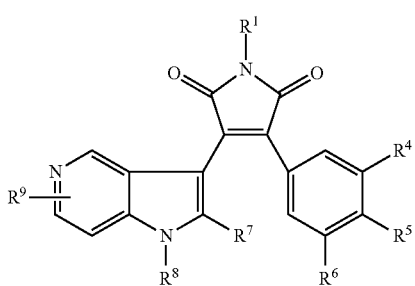

(Id)

wherein $R^1$, and $R^4$ to $R^9$ are as defined above.

According to a further embodiment, the present invention relates to the compounds of formula (Ie):

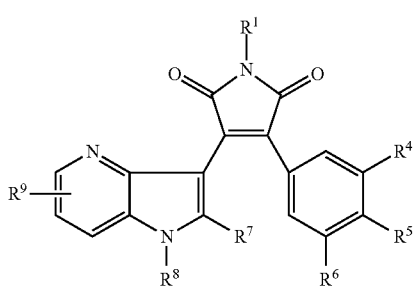

(Ie)

wherein $R^1$, and $R^4$ to $R^9$ are as defined above.

According to a further embodiment, $R^1$ and $R^7$ are independently of each other H or $C_1$-$C_6$-alkyl, and, in particular H.

According to a further embodiment, $R^9$ is H, $C_1$-$C_6$-alkyl or halogen and in particular H.

According to a further embodiment, $R^{10}$ is selected from
a) amino,
b) $C_1$-$C_6$-alkylamino,
c) di-$C_1$-$C_6$-alkylamino,
d) hydroxy,
e) $C_1$-$C_6$-alkoxy, and
f) saturated heterocyclyl with 5 or 6 ring atoms containing a nitrogen heteroatom and optionally 1 or 2 additional heteroatoms which are independently selected from O, N and S, wherein the heterocyclyl is attached to the $C_1$-$C_6$-alkyl group via the nitrogen atom and may carry an additional $C_1$-$C_6$-alkyl substituent at a carbon atom or a nitrogen atom.

According to a further embodiment, $R^{10}$ is selected from
a) amino,
b) $C_1$-$C_6$-alkylamino,
c) di-$C_1$-$C_6$-alkylamino,
d) hydroxy, and
e) $C_1$-$C_6$-alkoxy.

According to a further embodiment, $R^{10}$ is selected from
a) amino,
b) $C_1$-$C_6$-alkylamino, and
c) di-$C_1$-$C_6$-alkylamino According to a further embodiment, $R^{10}$ is selected from
d) hydroxy, and
e) $C_1$-$C_6$-alkoxy.

According to a further embodiment, $R^{10}$ is
f) saturated heterocyclyl with 5 or 6 ring atoms containing a nitrogen heteroatom and optionally 1 or 2 additional heteroatoms which are independently selected from O, N and S, wherein the heterocyclyl is attached to the $C_1$-$C_6$-alkyl group via the nitrogen atom and may carry an additional C1-C6-alkyl substituent at a carbon atom or a nitrogen atom;

According to a further embodiment, $R^{10}$ is selected from
g) phenoxy, and
h) benzyloxy.

According to a further embodiment, $R^{10}$ is selected from
i) $R^{11}CONR^{12}$—, and
j) $NR^{12}R^{12}CO$—.

According to a further embodiment, $R^{10}$ is selected from
k) $C_1$-$C_6$-alkyl-NHCONH—,
l) $C_1$-$C_6$-alkyl-NHCOO—, and
m) $C_1$-$C_6$-alkyl-OCONH—.

According to a further embodiment, $R^{10}$ is selected from
n) $R^{12}$—$OSO_2O$—,
o) $R^{11}SO_2O$—,
p) $R^{12}$—$OSO_2$—, and
q) $R^{11}SO_2$—.

According to a further embodiment, $R^{10}$ is selected from
r) $(R^{12}O)_2P(O)O$—,
s) $(R^{12}O)_2P(O)$—, and
t) $(R^{12}O)R_{11}P(O)O$—.

According to a further embodiment, a compound of the invention is a compound of formula II, formula III or formula IV:

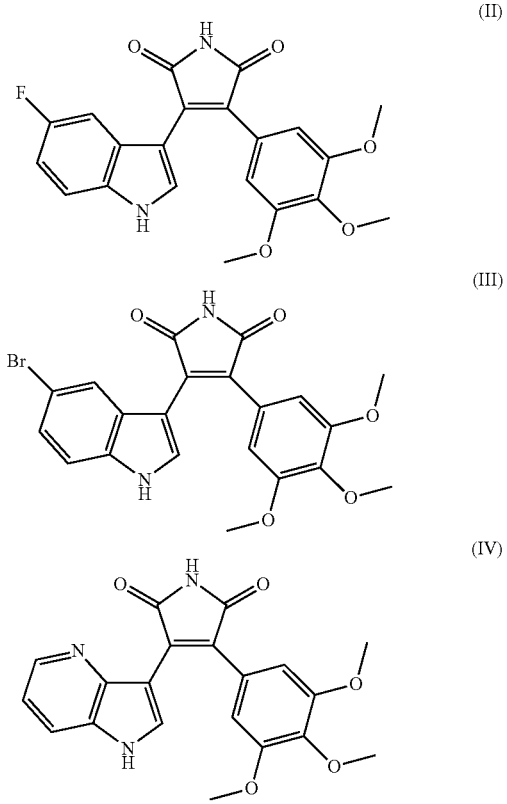

The compounds of the present invention can be prepared according to known methods, for example according to the methods, which are disclosed in WO 02/38561, EP 328 026, WO 03/095452, WO 03/103663 and WO 2006/061212. For the purposes of the present invention a modified procedure reported in *Tetrahedron Letters* (1999) 40: 1109-1112 has been proven to be particularly efficient. This procedure can be illustrated by the following reaction sequence:

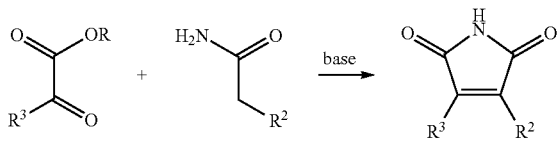

An indole glyoxyl ester is reacted with a phenyl acetamide derivative in a one-pot reaction in an inert solvent in the presence of a strong base. Preferably an ether is used as an inert solvent, such as tetrahydrofurane or dioxane. As a base potassium t-butoxide can for example be used. The water formed during the reaction is removed, for example by using a molecular sieve. The phenyl acetamides used as starting material are readily available from the corresponding acetic acids which are converted to the acid chloride and hydrolyzed with ammonia. The indole glyoxyl esters (R=methyl, ethyl) were synthesized by Friedel-Crafts-type acylation of the corresponding indole derivative with methyl or ethyl oxalyl chloride, cf. *Tetrahedron* 1999, 55 (43), 12577-12594. The corresponding azaindole glyoxyl esters can be prepared according to the method reported in *J. Org. Chem.* 2002, 67, 6226-6227 or by Friedel-Crafts acylation in the presence of aluminum chloride, cf. *Organic Letters* (2000) vol. 2, no. 10, 1485-1487.

The 4- and 6-azaindole starting compounds can be prepared by reacting 2-chloro-3-nitropyridine or 3-nitro-4-chloropyridine with vinyl magnesium bromide to give the 7-chloro-substituted 4- or 6-azaindole. The chloro substituent is then removed by catalytic hydrogenation. Said reactions are carried out as described in *J. Org. Chem.* 67, 2345-2347 (2002) and *J. Heterocycl. Chem.* 29, 359-363 (1992). The 4-azaindole starting compound can also be synthesized according to the procedures disclosed in Org. Biomol. Chem. 3, 20, 3701-3706 (2005).

The 5- and 7-azaindole starting compounds can be prepared by reacting 2- or 4-aminopyridine with di-tert-butyldicarbonate to 2- or 4-t-butoxycarbonylaminopyridine which is then reacted with methyl iodide and dimethylformamide in the presence of t-butyl lithium. The obtained product is then treated with a strong acid to give 5- or 7-azaindole. Said reactions are described in *Synthesis* 7, 877-882 (1996).

The compounds of the present invention have antineoplastic activity and can therefore be used for the treatment or prevention of tumors, in particular solid tumors, such as astrocytoma, bladder cancer, bone cancer, brain tumor, breast cancer, bronchial tumor, cervical cancer, colorectal cancer, endometrial cancer, esophageal cancer, gallbladder cancer, gastrointestinal stromal tumor, germ cell tumor, glioma, head and neck cancer, liver cancer, lymphoma, sarcoma, lung cancer, melanoma, ovarian cancer, pancreatic cancer, thyroid cancer, neuroblastoma, prostate cancer, renal cancer, skin cancer, squamous neck cancer, stomach (gastric) cancer, testicular cancer. The compounds of the invention are especially useful for treatment or prevention of cervical cancer, colorectal cancer, gastrointestinal stromal tumor, liver cancer, lung cancer, ovarian cancer, prostate cancer, stomach cancer, and pancreatic carcinoma.

According to a further embodiment, the compounds of the present invention can be used for the treatment or prevention of leukemia. Leukemia according to the present invention comprises in particular acute lymphocytic leukemia (also known as acute lymphoblastic leukemia, or ALL), acute myelogenous leukemia (also known as acute myeloid leukemia, or AML); chronic lymphocytic leukemia (CLL), mixed-lineage leukemia and chronic myelogenous leukemia (CML). These leukemias and further subtypes of these leukemias are defined by morphological, histochemical and immunological techniques that are well known by those skilled in the art.

In a further embodiment, the invention relates to the treatment of AML or ALL.

In a further embodiment of the invention, the leukemia is characterized by leukemic cells which are positive for expression of FLT3. In a particular embodiment of the invention, the leukemia is characterized by leukemic cells which show enhanced expression of FLT3, campared to non-malignant cells of the same cell type.

A further embodiment of the invention is a combination of the compounds of the present invention with one or more than one chemotherapeutic agent including antineoplastic agents, multidrug resistance reversing agents; and biological response modifiers, and combinations thereof, examples being given below.

Suitable antineoplastic agents may be selected from the group comprising compounds affecting integrity and synthesis of DNA, e.g. topoisomerase I inhibitors; alkylating agents: intercalating agents or DNA-binding antibiotics; antimitotic compounds such as taxanes: vinca alkabids or colchicine derivatives; compounds for targeted cancer therapy such as protein kinase inhibitors, antibodies binding to cell membrane receptors and soluble decoy receptors; compounds affecting the cell metabolism, e.g. farnesyltransferase inhibitors, purin or pyrimidin analogues.

Examples for antineoplastic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguanine), tipifarnib.

Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin and enzastaurin.

Examples for antineoplastic agents which are antibodies comprise trastuzumab, cetuximab, panitumumab, rituximab, bevacizumab, mapatumumab, conatumumab, lexatumumab and the like.

An example for a multidrug resistance reversing agent is PSC 833, a potent inhibitor of the efflux of antitumor drugs mediated by P-glycoprotein.

Suitable biological response modifiers may be selected from the group consisting of monoclonal antibodies and cytokines, such as interferons, interleukins and colony-stimulating factors, e.g., rituxan, CMA-676, interferon-alpha recombinant, interleukin-2, interleukin-3, erythropoetin, epoetin, G-CSF, GM-CSF, filgrastim, sargramostim and thrombopoietin.

According to a particular embodiment, the further chemotherapeutic agent is a topoisomerase I inhibitor and especially camptothecin or a derivative thereof such as described by Pommier, Y. (2006), Nature Reviews Cancer 6: 789-802. Examples for topomerase I inhibitors comprise compounds such as irinotecan (in particular irinotecan hydrochloride), topotecan (in particular topotecan hydrochloride), rubitecan, exatecan (in particular exatecan mesylate), lurtotecan, gimatecan, prothecan, karenitecin, belotecan (in particular belotecan hydrochloride), silatecan or diflomotecan and the salts thereof.

The weight ratio of the compounds of the invention to the chemotherapeutic agent is in general in the range from 5:1 to 1:500, in particular 3:1 to 1:200.

The combination of the invention exhibits enhanced tumor activity.

A further embodiment of the invention is a pharmaceutical composition comprising a compound of formula I, II, III or IV or a combination thereof with an additional chemotherapeutic agent as defined above. In general, the pharmaceutical compositions comprise an amount therapeutically effective for tumor treatment of a compound of formula I, II, III or IV or a combination as above-defined.

A further embodiment of the invention is a compound of formula I, II, III or IV for use in a method of treating tumors.

According to a further embodiment, said method comprises the use of an additional therapeutic agent (other than a compound of formula I, II, III or IV). The additional therapeutic agent may be as defined above.

For use the compounds or combinations of the present invention can be incorporated into standard pharmaceutical dosage forms. For example, the compounds or combinations are useful when administered in systemic or local, oral or parenteral applications and for this purpose are combined with the usual pharmaceutical excipients, diluents and adjuvants, e.g., organic and inorganic inert carrier materials such as water, gelatin, lactose, starch, magnesium stearate, talc, vegetable oils, gums, polyalkyleneglycols, etc. These pharmaceutical preparations can be employed in a solid form, e.g., as tablets, capsules, and especially in combination with or for admixture with a palatable food item suitable for mammals; or they can be administered in liquid form, e.g., as solutions and elixirs. Pharmaceutical excipients and adjuvants which can be added to include preservatives, antioxidants, antimicrobial agents and other stabilizers; wetting, emulsifying, and suspending agents, and anticaking compounds; fragrance and coloring additives; compositions for improving compressibility, or to create a delayed-, sustained-, or controlled-release of the active ingredient; and various salts to change the osmotic pressure of the pharmaceutical preparation or to act as buffers.

The therapeutically effective amount of a compound of Formula I, II, III or IV or combination as defined may be administered systemically to said mammal, wherein said systemic administration comprises: (1) injection or infusion into suitable body tissues or cavities of a pharmaceutical composition containing said compound or combination in suitable liquid form such as aqueous solutions, emulsions or suspensions for intraarterial, intra- or transdermal (including subcutaneous) and most commonly intramuscular or intravenous delivery thereof; or for serving as a depot for delivery thereof; (2) instillation into suitable body tissues or cavities of a pharmaceutical composition containing said compound or combination in suitable solid form, e.g., comprising a matrix of bio-compatible and bio-erodible materials in which particles of a compound of Formula I, II, III or IV or combination are dispersed for serving as a solid implant composition for delayed-, sustained-, and/or controlled-release delivery thereof; or (3) ingestion or administration of a pharmaceutical composition containing said compound or combination in suitable solid or liquid form for transdermal delivery thereof, for instance a transdermal patch or a subepidermal (subcuticular) implant, for peroral delivery thereof.

The dosage forms described herein may be formulated so as to provide controlled-, sustained, and/or delayed release of the active ingredient from said dosage form.

Preferred peroral dosage forms for systemic administration are solids, e.g., palatable oral compositions such as fast dissolving palatable wafers, tablets, capsules, caplets, etc., and liquids, e.g., solutions, suspensions, emulsions, etc. Pharmaceutical compositions of special types suitable for oral administration to mammals may be used, and include, but are not limited to such items as an oral paste to be delivered to the back of the tongue of the mammal being treated, a granular form to be delivered through incorporation in the mammal's food, and a chewable form wherein the active ingredient is consumed along with the palatable chew, or a chewable form which may deliver the active ingredient by leaching from the body of the chew which is not consumed, during mastication by the mammal being treated. Tablets and capsules are preferred dosage forms.

Said therapeutically effective amount of a compound of Formula I, II, III or IV or combination as defined may also be administered locally to said mammal, wherein said local administration comprises: (1) injection or infusion into a local site affected with abnormal angiogenesis and/or vascular dysfunction of a pharmaceutical composition containing said compound of formula (I) or combination in suitable liquid form for delivery thereof, including components which provide delayed-release, controlled-release, and/or sustained-release of said compound or combination into said local site; or for serving as a depot for delivery thereof wherein said composition provides storage of said compound or combination and thereafter delayed-, sustained-, and/or controlled-release thereof; or (2) instillation of a pharmaceutical composition containing said compound or combination in suitable solid form for serving as a solid implant for delivery thereof, said composition optionally providing delayed-, sustained-, and/or controlled-release of said compound or combination to said local site.

The therapeutically effective amount of the compound of Formula I, II, III or IV is administered to a mammal to be treated in an amount expressed as milligrams per $m^2$ of body surface of said mammal, per day: "mg/$m^2$/day". The dose, i.e., the therapeutically effective amount of a compound of Formula I, II, III or IV will usually range from about 0.2 mg/$m^2$/day to about 2000 mg/$m^2$/day, preferably from about 0.5 mg/$m^2$/day to about 1500 mg/$m^2$/day, more preferably from about 1.0 mg/$m^2$/day to about 1000 mg/$m^2$/day. In case of a combination of a compound of formula I with a chemotherapeutic agent such as an anticancer agent, administration may be simultaneously, for example given as coformulation or separately, or sequentially. The dose of a compound of formula I, II, III or IV will usually be as given above whereas the dose of the chemotherapeutic agent will range from about 0.2 mg/$m^2$/day to about 2000 mg/$m^2$/day, preferably from about 0.5 mg/$m^2$/day to about 1500 mg/$m^2$/day, more preferably from about 1.0 mg/$m^2$/day to about 1000 mg/$m^2$/day.

It is necessary for the skilled artisan, not only to determine the preferred route of administration and the corresponding dosage form and amount, but said artisan must also determine the dosing regimen, i.e., the frequency of dosing. In general terms it is most likely that the choice will be between once-a-day (s.i.d.) dosing and twice-a-day (b.i.d.) dosing, and that the former will provide more rapid and profound therapy, while the latter will provide less profound but more sustained therapy.

The antineoplastic activity of the compounds or combinations of the present invention was determined by the following assays:

Evaluation of Antiproliferative Effect (MTT Assay)

Antiproliferative activity of test compounds was determined by the 3-(4,5-dimethylthiazol-2-yl)-2,5-diphenyltetrazolium bromide (MTT) assay as described previously (Mosmann, T. et al. (1983) *J. Immunol. Methods* 65, 55-63). Cells in the exponential growth phase were transferred to 96-well flat-bottomed plates. Cell suspensions (200 µl) containing 10,000 viable cells were plated into each well and incubated over night before exposure with various concentrations of agents. Cells were then incubated with 100 µl of different concentrations of compounds for 3 days at 37° C. with 5% $CO_2$. At the end of the time point (3 days), 10 µl/well of MTT stock solution (5 mg/ml) (Biomol, Germany) were added. Cells were then incubated at 37° C. with 5% $CO_2$ for 4 hours. 100 µl of solubilization solution (10% SDS in 0.01M HCl) were added and cells were incubated at 37° C. with 5% $CO_2$ over night. Plates were read on an ELISA-Reader ELX 800 (BIO-TEK Software KC 4) at 562 nm absorbance. Each experiment was done in triplicate.

Nicoletti Apoptosis Assay by Cell Cycle Analysis

Cancer cells were transferred to 12-well flat-bottomed plates. Cell suspensions (1 ml) containing 1.5×$10^5$ viable cells were plated into each well and incubated over night before exposure with various concentrations of agents. Cells were then incubated in 1 ml medium with various concentrations of single applied moguntinones, irinotecan alone, or with the combinations of moguntinones with irinotecan or topotecan at 37° C. with 5% $CO_2$.

After incubation cells were washed with PBS, trypsinizated, palleted and mixed with propidium-iodide-buffer (containing 0.1% sodium citrate, 0.1% triton X-100, 50 mg/ml propidium-iodide) and incubated for 1 hour at 4° C. Cell cycle sub-G1-fraction analysis was performed as described previously[23] using a FACS cytometer (BD FACS Calibur™, BD Biosciences, Heidelberg, Germany). Each experiment was done in triplicate.

GSK-3β, VEGFR-2, FLT-3, CHK1 kinase assay $IC_{50}$-values were carried out at Millipore UK Ltd; Gemini Crescent; Dundee Technology Park; Dundee DD2 1SW; UK ($IC_{50}$Profiler). http://www.millipore.com/drugdiscovery/svp3/kpservices Details of each assay protocol can be found on Millipore's website at www.millipore.com/drugdiscovery/dd3/assayprotocols.

Other kinase assay data are from Peifer et al. *J. Med. Chem.* 2006, 49, 7549-7553 peformed by ProQinase GmbH, Freiburg, Germany.

Drugs 26 mmol/l working solutions of the test compounds in DMSO were prepared and stored in aliquots at –20° C. Irinotecan and Topotecan were obtained from the Pharmacy of the University Hospital of Mainz, dissolved in water. Stock solutions were prepared at 29.6 mmol/l for irinotecan and 4.75 mmol/l for topotecan and stored in aliquots at 4° C. The drugs were diluted in culture medium to obtain the desired concentrations immediately before use.

Cell Line

The human colon cancer cell lines HCT-116, HT-29, Caco-2, SW480 and the stomach cancer cell line MKN-45 were obtained from the DSMZ, Germany. HCT-116, HT-29 and SW480 cells were routinely cultured in RPMI 1640 supplemented with 10% FCS, MKN-45 in RPMI 1640 supplemented with 20% FCS and Caco-2 cells in 80% MEM (with Earle's salts)+20% FCS+non-essential amino acids. All cells were maintained at 37° C. in an incubator under an atmosphere containing 5% $CO_2$. After incubation the cells were washed with PBS, trypsinized, pelleted and mixed with PI buffer (containing 0.1% sodium citrate, 0.1% triton X-100, 50 mg/ml propidium iodide (PI)) and incubated for 1 hour at 4° C. Cell cycle sub-G1 fraction analysis was performed as described previously (Nicoletti, I. et al. (1991) *J. Immunol. Methods* 139, 271-279) using a flow cytometer (BD FACS Calibur™, BD Biosciences, Heidelberg, Germany). Each experiment was done in triplicate.

The same analysis was performed with HUVEC cells. 1.5× $10^4$ cells were plated into each well and treated with test compounds for 4 days.

In Vitro Investigation of Antineoplastic Properties of the Compounds of the Invention The antitumor efficacy of the compounds of the invention was examined against HT-29 human colon adenocarcinoma cells. The tested compounds showed initial dose dependent cytotoxicity when used in concentrations up to low micromolar range (Table 1). The compound of example 1 of WO 2006/061212 was used as comparative compound.

TABLE 1

Decrease of HT-29 colon cancer cell viability (%) under treatment with compounds of the invention for 3 days detected in MTT-assay

| Compound | WO 2006/ 061212 Ex. 1 | Example 1 | Example 2 | Example 5 | Example 6 | Example 3 | Example 4 | Example 8 | Example 7 | Example 9 |
|---|---|---|---|---|---|---|---|---|---|---|
| 2.6 µM | 78.5 ± 3.7 | 32.29 ± 1.07 | 45.77 ± 3.25 | 68.48 ± 8.69 | 39.33 ± 2.60 | 68.80 ± 2.48 | 37.85 ± 1.30 | 81.14 ± 2.99 | 86.50 ± 2.16 | 66.45 ± 3.10 |
| 7.9 µM | 62.9 ± 1.5 | 29.32 ± 2.09 | 36.44 ± 1.77 | 52.60 ± 0.53 | 38.54 ± 2.43 | 70.21 ± 3.72 | 34.70 ± 0.78 | 84.14 ± 2.18 | 56.92 ± 3.02 | 49.90 ± 1.32 |
| 26 µM | 53.9 ± 4.8 | 12.50 ± 0.39 | 17.65 ± 0.13 | 32.16 ± 0.90 | 15.81 ± 1.35 | 45.73 ± 2.18 | 27.73 ± 1.23 | 53.39 ± 0.10 | 20.14 ± 1.36 | 22.58 ± 1.16 |
| 52 µM | 42.8 ± 1.6 | 8.95 ± 0.65 | 6.68 ± 0.29 | 15.00 ± 0.90 | 19.41 ± 1.32 | 28.70 ± 0.55 | 25.45 ± 2.26 | 39.33 ± 1.31 | 24.34 ± 0.98 | 15.32 ± 1.21 |

Viability of untreated HT-29 cells: 100%

In additional studies the effect of several compounds of formula I (examples 1 to 9) in combination with irinotecan was determined. The results are shown in table 2.

TABLE 2

Enhancement of apoptosis in human HT-29 cancer cells by combining compounds of formula I with irinotecan

| Compound | Example 1 | Example 2 | Example 5 | Example 6 | Example 3 | Example 4 | Example 8 | Example 7 | Example 9 |
|---|---|---|---|---|---|---|---|---|---|
| Single-agent treatment with 7.9 µM of comp . . . | 5.69 ± 0.69 | 4.01 ± 0.66 | 2.50 ± 1.73 | 3.17 ± 0.86 | 8.08 ± 0.77 | 11.25 ± 0.11 | 10.01 ± 2.16 | 4.64 ± 0.75 | 3.01 ± 0.40 |
| Combination compound . . . plus Irinotecan 1.18 µM | 51.00 ± 0.56 | 56.01 ± 0.29 | 43.48 ± 1.87 | 50.28 ± 1.31 | 71.28 ± 3.51 | 65.71 ± 0.04 | 56.81 ± 3.96 | 62.32 ± 1.63 | 49.49 ± 1.82 |

Induction of apoptosis under Irinotecan single application 18.3 ± 1.1%
Induction of apoptosis by agent-free control 3.4 ± 0.9%

The observed synergistic effect allows the dosage reduction of the chemotherapeutic agents (resulting in better tolerance), enhances their potency and abrogates the development of resistance.

The following examples illustrate the invention without limiting it.

EXAMPLES

Infrared spectra were recorded on a Thermo Nicolet Avatar 330 FT-IR spectrometer. 1H (300 MHz, digital resolution 0.3768 Hz) and 13C (75 MHz, digital resolution 1.1299 Hz) NMR were recorded on a Bruker AC 300: the data are reported as follows: chemical shift in ppm from Me$_4$Si as external standard, multiplicity and coupling constant (Hz). EI-Mass spectra were recorded on a Varian MAT 44S (80 eV) and FD-Mass spectra on a Finnigan MAT 7 (5 kV). For clarity only the highest measured signal is given for FD-Mass spectra. Elemental analyses were performed on a Haereus CHN rapid, Carlo Erba Strumentazione 1106. Combustion analyses agreed with the calculated data within ±0.4 unless otherwise stated. Melting points/decomposition temperatures were determined on a Büchi apparatus according to Dr. Tottloi and are uncorrected. Where appropriate, column chromatography was performed for crude precursors with Merck silica gel 60 (0.063-0.200 mm). Column chromatography for test compounds was performed using a MPLC-System B-680 (Büchi) with Merck silica gel (0.015-0.040 mm). The progress of the reactions was monitored by thin layer chromatography (TLC) performed with Merck silica gel 60 F-254 plates. Where necessary, reactions were carried out in a nitrogen atmosphere using 4 Å molecular sieves. All reagents and solvents were obtained from commercial sources and used as received.

General procedure 1 for the preparation of N-1 substituted indole-3-ethylglyoxylate A modified procedure of Faul et al., *J. of Organic Chemistry* 1998, 63, 6, 1961-1973 and Zhang et Al., *Bioorg. Med. Chem. Lett.*, 2004, 14, 12, 3245-3250 was used. A stirred suspension of indole-3-ethylglyoxylate (1 equiv.), CsCO$_3$ or K$_2$CO$_3$ (1.3 equiv.) and the corresponding aliphatic bromo- or chloro-substituent in dry DMF was heated to 75-80° C. under nitrogen for 8 hours. The reaction was cooled to RT, diluted with ethyl acetate (40 ml) and filtered over Celite®. The mixture was washed with water (4×40 ml). The organic phase was dried over Na$_2$SO$_4$, filtered, concentrated and purified by column chromatography.

General procedure 2 for the preparation of 3-phenyl-4-indolyl-maleinimides

The procedure of Peifer et al., WO 2006/061212 and *J. Med. Chem.* 2006, 49, 4, 1271-1281, was used to prepare 3-phenyl-4-indolyl-maleinimides.

Example 1

3-(1-[2-Ammonioethyl]-1H-indol-3-yl)-4-(3,4,5-trimethoxyphenyl)-maleinimide-chloride

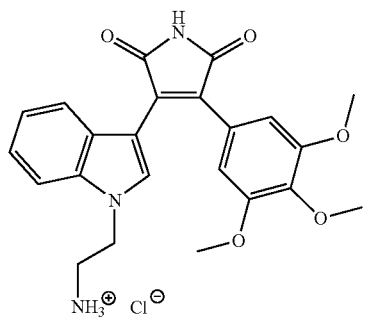 [SMILES: COc1cc(C2=C(c3cn(CC[NH3+])c4ccccc34)C(=O)NC2=O)cc(OC)c1OC ; [Cl-]]

A modified procedure of Wescott et al., *J. Org. Chem.* 2003, 68, 26, 10058-10066, was used to prepare tert.-butyl 2-bromoethylcarbamate. A solution of NaHCO$_3$ (24.4 mmol; 2.0 g) in 80 ml water and a solution of di-tert.-butyldicarbonate (24.4 mmol; 5.33 g) in 50 ml were added to a stirred suspension of 2-bromoethylammonium-bromide (24.4 mmol; 5.0 g) in 100 ml chloroform. The reaction was refluxed for 5 hours. After cooling to RT (room temperature) the organic phase was separated and aqueous phase was extracted with chloroform. The combined organic layers were dried over Na$_2$SO$_4$, filtered, concentrated and purified by column chromatography. Tert.-butyl 2-bromoethylcarbamate (6.86 mmol, 28.2%) was obtained as a colorless oil. $^1$H NMR (300 MHz, CDCl$_3$) 4.98 (bs; 1H; NH); 3.52 (dd; J=5.3 Hz; J=11.0 Hz; 2H; CH$_2$N); 3.44 (t; J=5.3 Hz; 2H; CH$_2$Br); 1.43 (s; 9H; C(CH$_3$)$_3$).

The general procedure 1 was then followed using the above product (6.68 mmol, 1.54 g), ethyl-2-(1H-indol-3-yl)-2-oxoacetate (6.68 mmol, 1.45 g) and Cs$_2$CO$_3$ (9.82 mmol, 3.20 g). The purification was achieved by column chromatography (petro-lether:ethylacetate:diethylamine 5:4:1) to yield ethyl-2-(1-{2-[(tert.-butoxycarbonyl)-amino]ethyl}-1H-indol-3-yl)-2-oxoacetate (4.54 mmol, 68%) as white crystals. Mp=114-115° C. IR ṽ [cm$^{-1}$]=3357; 2977; 1727; 1686; 1638; 1518. EI-MS (m/z)=360 (7.59%; M$^{+\cdot}$). $^1$H NMR (300 MHz, CDCl$_3$) 8.44 (m; 1H; indole-H); 8.34 (s; 1H; indole-H); 7.42 (m; 1H; indole-H); 7.35 (m; 1H; indole-H); 4.63 (bs; 1H; NH); 4.37 (m; 4H; OCH$_2$CH$_3$; indole-CH$_2$); 3.54 (q; $^3$J=6.2 Hz; 2H; CH$_2$—N); 1.43 (t; 3H; $^3$J=7.1 Hz; OCH$_2$CH$_3$); 1.43 (s; 9H; C(CH$_3$)$_3$).

The general procedure 2 was then followed using ethyl-2-(1-{2-[(tert.-butoxycarbonyl)amino]ethyl}-1H-indol-3-yl)-2-oxoacetate (2 mmol, 0.77 g), 3,4,5-trimethoxyphenylacetamide (1.8 mmol, 0.41 g) and 1 M tert.-BuOK (6 mmol, 6 ml). The purification was achieved by column chromatography (petrolether:ethylacetate 4:6) to yield 3-(1-{2-[(tert.-butoxycarbonyl)amino]ethyl}-1H-indol-3-yl)-4-(3,4,5-trimethoxyphenyl)-maleinimide (0.8 mmol, 43%) as orange crystals. Mp 97-98° C. IR ṽ [cm$^{-1}$]=3300; 2987; 1698. EI-MS m/z (rel. int.)=521 (91.98%; M$^{+\cdot}$). $^1$H NMR (300 MHz, CDCl$_3$) 7.92 (s; 1H; indole-H); 7.36 (m; 1H; indole-H); 7.35 (bs; 1H; imide-NH); 7.17 (t; $^3$J=7.2 Hz; 1H; indole-H); 6.86 (t; $^3$J=7.2 Hz; 1H; indole-H); 6.78 (s; 2H; 2×Ar—H); 6.46 (d; $^3$J=8.1 Hz; 1H; indole-H); 4.63 (bs, 1H; NH); 4.36 (t; $^3$J=5.78 Hz; 2H; indole-CH$_2$); 3.86 (s; 3H; OCH$_3$); 3.55 (m; 2H; CH$_2$N); 3.49 (s; 6H; 2×OCH$_3$); 1.44 (s; 9H; C(CH$_3$)$_3$).

A stirred solution of 3-(1-{2-[(tert.-butoxycarbonyl) amino]ethyl}-1H-indol-3-yl)-4-(3,4,5-trimethoxyphenyl)-maleinimide (0.8 mmol, 0.4 g) in 50 ml ethanol and 2.3 M ethanolic HCl (3.42 mmol, 1.5 ml) was heated to 80° C. for 3 hours. The precipitate was filtered and washed with ethanol to give the title compound (0.66 mmol, 86%) as red crystals. Mp 277.1° C. IR ṽ [cm$^{-1}$]=3151; 2977; 1698. FD-MS m/z (rel. int.)=423.5 (1.2%; M$^{+\cdot}$). $^1$H NMR (300 MHz, CDCl$_3$) 11.12 (bs; 1H; imide-NH); 8.14 (bs; 3H; NH$_3$); 8.10 (s; 1H; indole-H); 7.63 (d; $^3$J=8.2 Hz; 1H; indole-H); 7.18 (t; $^3$J=7.3 Hz; 1H; indole-H); 6.82 (t; $^3$J=7.3 Hz; 1H; indole-H); 6.73 (s; 2H; 2×Ar—H); 6.38 (d; $^3$J=8.2 Hz; 1H; indole-H); 4.55 (t; $^3$J=6.6 Hz; 2H; indole-CH$_2$); 3.66 (s; 3H; OCH$_3$); 3.38 (s; 6H; 2×OCH$_3$); 3.25 (m; 2H; CH$_2$N). Anal. calcd for C$_{23}$H$_{24}$ClN$_3$O$_5$: C, 60.33; H, 5.28; N, 9.18. Found: C, 60.36; H, 5.29; N, 9.09.

Example 2

3-(1-[3-Ammoniopropyl]-1H-indol-3-yl)-4-(3,4,5-trimethoxyphenyl)-maleinimide-chloride

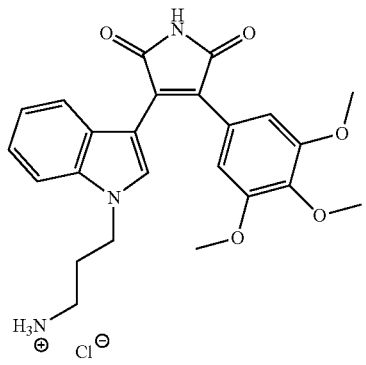 [SMILES: COc1cc(C2=C(c3cn(CCC[NH3+])c4ccccc34)C(=O)NC2=O)cc(OC)c1OC ; [Cl-]]

Tert.-butyl-(3-bromopropyl)carbamate (7.14 mmol, 78%) was synthesized using the same procedure as for example 1. $^1$H NMR (300 MHz, CDCl$_3$) 4.73 (bs, 1H; NH); 3.41 (t; $^3$J=6.5 Hz; 2H; CH$_2$Br); 3.24 (m; 2H; CH$_2$N); 2.02 (quint; $^3$J=6.5 Hz; 2H; CH$_2$CH$_2$CH$_2$); 1.41 (s; 9H; C(CH$_3$)$_3$).

The general procedure 1 was then followed using the above product (7.14 mmol, 1.7 g), ethyl-2-(1H-indol-3-yl)-2-oxoacetate (4.6 mmol, 1.0 g) and Cs$_2$CO$_3$ (9.21 mmol, 3.0 g). The purification was achieved by column chromatography (petrol-ether:ethylacetate 1:1) to yield ethyl-2-(1-{3-[(tert.-butoxycarbonyl)amino]propyl}-1H-indol-3-yl)-2-oxoacetate (5.3 mmol, 74%) as pale yellow crystals. Mp 89-90° C. IR ṽ [cm$^{-1}$]=3392; 2977; 2936; 1727; 1698; 1619; 1515. EI-MS m/z (rel. int.)=374 (8.9%; M$^{+\cdot}$). $^1$H NMR (300 MHz, CDCl$_3$) 8.45 (m; 2H; indole-H); 7.35 (m; 3H; indole-H); 4.63 (bs; 1H; NH); 4.41 (q; $^3$J=7.1 Hz; 2H; OCH$_2$CH$_3$); 4.24 (t; $^3$J=7.1 Hz; 2H; indole-CH$_2$); 3.18 (q; $^3$J=6.1 Hz; 2H; CH$_2$N); 2.09 (m; 2H; CH$_2$CH$_2$CH$_2$); 1.44 (s; 9H; C(CH$_3$)$_3$); 1.43 (t; $^3$J=7.1 Hz; 3H; OCH$_2$CH$_3$).

The general procedure 2 was then followed using ethyl-2-(1-{3-[(tert.-butoxycarbonyl)amino]propyl}-1H-indol-3-yl)-2-oxoacetate (6.8 mmol, 2.5 g), 3,4,5-trimethoxyphenylacetamide (6.8 mmol, 1.5 g) and 1 M tert.-BuOK (14.4 mmol, 14.4 ml). The purification was achieved by column chromatography (petrolether:ethylacetate 1:1) to yield 3-(1-{3-[(tert.-butoxycarbonyl)amino]propyl}-1H-indol-3-yl)-4-(3,4,5-trimethoxyphenyl)-maleinimide (2.5 mmol, 36.8%) as orange crystals. Mp 178-179° C. IR ṽ [cm$^{-1}$]=3408; 1714; 1689; 1613; 1515. FD-MS m/z (rel. int.)=535.5 (100%). $^1$H NMR (300 MHz, CDCl$_3$) 7.95 (s; 1H; indole-H); 7.60 (bs; 1H; imide-NH); 7.32 (d; $^3$J=8.2 Hz; 1H; indole-H); 7.16 (t; $^3$J=7.2 Hz; 1H; indole-H); 6.85 (t; $^3$J=7.2 Hz; 1H; indole-H); 6.79 (s; 2H; 2×Ar—H); 6.47 (d; $^3$J=8.2 Hz; 1H; indole-H); 4.65 (bs; 1H; NH); 4.26 (t; $^3$J=7.10 Hz; 2H; indole-CH$_2$); 3.85 (s; 3H; OCH$_3$); 3.49 (s; 6H; 2×OCH$_3$); 3.16 (m; 2H; CH$_2$N); 2.11 (m; 2H; CH$_2$CH$_2$CH$_2$); 1.44 (s; 9H; C(CH$_3$)$_3$).

A stirred solution of 3-(1-{3-[(tert.-butoxycarbonyl) amino]propyl}-1H-indol-3-yl)-4-(3,4,5-trimethoxyphenyl)-maleinimide (2.5 mmol, 1.32 g) in 150 ml ethanol and 2.3 M ethanolic HCl (11.25 mmol, 4.9 ml) was heated to 80° C. for 3 hours. The precipitate was filtered and washed with ethanol to give the title compound (2.2 mmol, 88%) as orange crystals. Mp 274-275° C. IR $\tilde{\nu}$ [cm$^{-1}$]=3145; 2958; 1761; 1708; 1597; 1499. EI-MS m/z (rel. int.)=438 (5.6%; M$^{+\cdot}$). $^1$H NMR (300 MHz, CDCl$_3$) 11.11 (s; 1H; imide-NH); 8.07 (s; 1H; indole-H); 7.96 (bs; 3H; NH$_3$); 7.62 (d; $^3$J=8.1 Hz; 1H; indole-H); 7.16 (t; $^3$J=7.7 Hz; 1H; indole-H); 6.80 (t; $^3$J=7.7 Hz; 1H; indole-H); 6.72 (s; 2H; 2×Ar—H); 6.36 (d; $^3$J=8.1 Hz; 1H; indole-H); 4.42 (t; $^3$J=6.7 Hz; 2H; indole-CH$_2$); 3.65 (s; 3H; OCH$_3$); 3.36 (s; 6H; 2×OCH$_3$); 2.75 (dd; 2H; $^3$J=6.7 Hz; $^3$J=12.3 Hz; CH$_2$N); 2.07 (m; 2H; CH$_2$CH$_2$CH$_2$). Anal. calcd for C$_{24}$H$_{26}$ClN$_3$O$_5$: C, 61.08; H, 5.55; N, 8.90. Found: C, 60.96; H, 5.35; N, 8.88.

Example 3

3-(1-[2-Hydroxyethyl]-1H-indol-3-yl)-4-(3,4,5-trimethoxyphenyl)-maleinimide

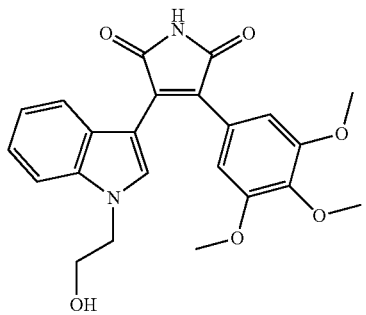 [SMILES: COc1cc(C2=C(c3cn(CCO)c4ccccc34)C(=O)NC2=O)cc(OC)c1OC]

A modified procedure of Galka et al., *J. Lab. Comp. Rad.* 2005, 48, 11, 797-809, was used. A mixture of 2-bromoethanol (6.6 mmol; 0.83 g=0.47 ml), tert.-butyldimethylsilylchloride (6.6 mmol, 1.0 g) and imidazole (7.3 mmol; 0.5 g) was stirred at RT for 3 hours under nitrogen atmosphere. The reaction was quenched with water, extracted with diethylether. The organic phases were dried over Na$_2$SO$_4$, filtered and concentrated. The purification was achieved by column chromatography (petrolether) to yield 2-bromoethoxy)(tert.-butyl)dimethylsilane (6.4 mmol, 96%). $^1$H NMR (300 MHz, CDCl$_3$) 3.91 (t; $^3$J=6.5 Hz; 2H; OCH$_2$); 3.41 (t; $^3$J=6.5 Hz; 2H; CH$_2$Br); 0.93 (s; 9H; C(CH$_3$)$_3$); 0.11 (s; 6H; 2×CH$_3$).

The general procedure 1 was then followed using the above product (6.4 mmol, 1.53 g), ethyl-2-(1H-indol-3-yl)-2-oxoacetate (5.99 mmol, 1.3 g) and Cs$_2$CO$_3$ (8.1 mmol, 2.63 g). The purification was achieved by column chromatography (petrol-ether:ethylacetate 7:3) to yield ethyl-2-(1-{2-[{1-(tert.-butyl)-1,1-dimethylsilyl}oxy]-ethyl}-1H-indol-3-yl)-2-oxoacetate (4.37 mmol, 73%) as pale yellow oil. IR $\tilde{\nu}$ [cm$^{-1}$]=2958; 2923; 2857; 1736; 1635; 1514; 1461. EI-MS m/z (rel. int.)=375 (6.0%; M$^{+\cdot}$). $^1$H NMR (300 MHz, CDCl$_3$) 8.45 (m; 1H; indole-H); 8.42 (s; 1H; indole-H); 7.37 (m; 3H; indole-H); 4.41 (q; $^3$J=7.1 Hz; 2H; OCH$_2$CH$_3$); 4.29 (t; $^3$J=5.1 Hz; 2H; indole-CH$_2$CH$_2$O); 3.95 (t; $^3$J=5.1 Hz; 2H indole-CH$_2$CH$_2$O); 1.43 (t; $^3$J=7.1 Hz; 3H; OCH$_2$CH$_3$); 0.80 (s; 9H; C(CH$_3$)$_3$); −0.17 (s; 6H; 2×CH$_3$).

The general procedure 2 was then followed using ethyl-2-(1-{2-[{1-(tert.-butyl)-1,1-dimethylsilyl}oxy]ethyl}-1H-indol-3-yl)-2-oxoacetate (1.8 mmol, 0.69 g), 3,4,5-trimethoxyphenylacetamide (1.6 mmol, 0.36 g) and 1 M tert.-BuOK (6 mmol, 6 ml). The purification was achieved by column chromatography (petrolether:ethylacetate 7:3) to yield 3-(1-{2-[{1-(tert.-butyl)-1,1-dimethylsilyl}oxy]ethyl}-1H-indol-3-yl)-4-(3,4,5-trimethoxyphenyl)-maleinimide (0.7 mmol, 39%) as an orange oil. IR $\tilde{\nu}$ [cm$^{-1}$]=3186; 2980; 2930; 2879; 1692. EI-MS m/z (rel. int.)=536 (68%; M$^+$). $^1$H NMR (300 MHz, CDCl$_3$) 8.06 (s; 1H; indole-H); 7.34 (d; $^3$J=8.1 Hz; 2H; indole-H); 7.29 (bs, 1H; imide-NH) 7.15 (t; $^3$J=7.5 Hz; 1H; indole-H); 6.84 (t; $^3$J=7.5 Hz; 1H; indole-H); 6.77 (s; 2H; Ar—H); 6.42 (d; $^3$J=8.1 Hz; 1H; indole-H); 4.31 (t; $^3$J=5.2 Hz; 2H; indole-CH$_2$CH$_2$O); 3.98 (t; $^3$J=5.2 Hz; 2H indole-CH$_2$CH$_2$O); 3.86 (s; 3H; OCH$_3$); 3.50 (s; 6H; 2×OCH$_3$); 0.82 (s; 9H; C(CH$_3$)$_3$); −0.13 (s; 6H; Si(CH$_3$)$_2$).

A modified procedure of Csuk et al., *Z. Naturforsch.*, 2003, 58b, 97-105, was used. Tetrabutylammoniumfluoride (0.79 mmol, 0.25 g) was added to a stirred solution of the above product (0.7 mmol, 0.26 g) in 10 ml THF (tetrahydrofurane). After the reaction was completed (TLC-control) (TLC=thin layer chromatography) it was concentrated. The purification was achieved by column chromatography (petrol-ether:ethylacetate:methano12:7:1) to yield 3-(1-[2-hydroxyethyl]-1H-indol-3-yl)-4-(3,4,5-trimethoxyphenyl)-maleinimide (0.4 mmol, 58%) as dark red crystals. Mp=195-196° C. IR $\tilde{\nu}$ [cm$^{-1}$]=3221; 1746; 1705. EI-MS m/z (rel. int.)=422 (100%; M$^{+\cdot}$). $^1$H NMR (300 MHz, CDCl$_3$) 8.02 (s; 1H; indole-H); 7.37 (d; $^3$J=7.9 Hz; 1H; indole-H); 7.32 (s; 1H; imide-NH); 7.17 (t; $^3$J=7.7 Hz; 1H; indole-H); 6.87 (t; $^3$J=7.7 Hz; 1H; indole-H); 6.79 (s; 2H; Ar—H); 6.50 (d; $^3$J=7.9 Hz; 1H; indole-H); 4.37 (t; $^3$J=5.2 Hz; 2H; indole-CH$_2$); 4.06 (q; $^3$J=5.0 Hz; 2H; CH$_2$O); 3.86 (s; 3H; OCH$_3$); 3.50 (s; 6H; 2×OCH$_3$). Anal. calcd for C$_{23}$H$_{22}$N$_2$O$_6$: C, 65.39; H, 5.25; N, 6.63. Found: C, 65.35; H, 5.33; N, 6.70.

Example 4

3-(1-[3-Hydroxypropyl]-1H-indol-3-yl)-4-(3,4,5-trimethoxyphenyl)-maleinimide

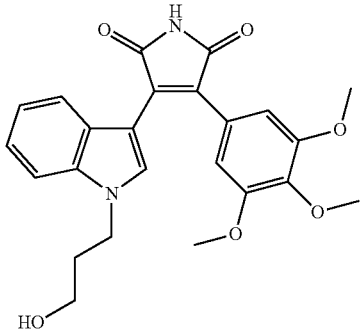 [SMILES: COc1cc(C2=C(c3cn(CCCO)c4ccccc34)C(=O)NC2=O)cc(OC)c1OC]

(3-Bromopropoxy)-tert.-butyldimethylsilane (36.4 mmol, 93%) was synthesized using the same procedure as for example 3. $^1$H NMR (300 MHz, CDCl$_3$) 3.73 (t; $^3$J=5.7 Hz; 2H; CH$_2$O); 3.51 (t; $^3$J=6.4 Hz; 2H; CH$_2$Br); 2.02 (q; $^3$J=5.7 Hz; $^3$J=6.4 Hz; 2H; CH$_2$CH$_2$CH$_2$); 0.89 (s; 9H; C(CH$_3$)$_3$); 0.06 (s; 6H; 2×CH$_3$).

The general procedure 1 was then followed using the above product (7.9 mmol, 2 g), ethyl-2-(1H-indol-3-yl)-2-oxoacetate (7.4 mmol, 1.61 g) and Cs$_2$CO$_3$ (10 mmol, 3.25 g). The purification was achieved by column chromatography (petrol-ether:ethylacetate 9:1) to yield ethyl-2-(1-{3-[{1-(tert.-butyl)-1,1-dimethylsilyl}oxy]-propyl}-1H-indol-3-yl)-2-oxoacetate (6.7 mmol, 91%) as pale yellow crystals. Mp=51-52° C. IR $\tilde{\nu}$ [cm$^{-1}$]=3142; 2958; 2924; 2867; 1727; 1638. EI-MS m/z (rel. int.)=389 (5.2%; M$^{+\cdot}$). $^1$H NMR (300 MHz, CDCl$_3$) 8.46 (m; 1H; indole-H); 8.37 (s; 1H; indole-H); 7.43 (m; 1H; indole-H); 7.34 (m; 2H; indole-H); 4.41 (q;

$^3$J=7.1 Hz; 2H; OCH$_2$CH$_3$); 4.33 (t; $^3$J=6.8 Hz; 2H; indole-CH$_2$); 3.58 (t; $^3$J=5.5 Hz; 2H; CH$_2$O); 2.06 (m; 2H; indole-CH$_2$CH$_2$CH$_2$O); 1.43 (t; J=7.1 Hz; 3H OCH$_2$CH$_3$); 0.94 (s; 9H); 0.07 (s; 6H).

The general procedure 2 was then followed using ethyl-2-(1-{3-[{1-(tert.-butyl)-1,1-dimethylsilyl}oxy]propyl}-1H-indol-3-yl)-2-oxoacetate (6.7 mmol, 2.64 g), 3,4,5-trimethoxyphenylacetamide (6.04 mmol, 1.36 g) and 1 M tert.-BuOK (18 mmol, 18 ml). The purification was achieved by column chromatography (petrol-ether:ethylacetate 7:3) to yield 3-(1-{3-[{1-(tert.-butyl)-1,1-dimethylsilyl}oxy]propyl}-1H-indol-3-yl)-4-(3,4,5-trimethoxyphenyl)-maleinimide (3 mmol, 45%) as yellow crystals. Mp=99-100° C. IR ṽ [cm$^{-1}$]=3202; 3066; 2955; 2923; 2854; 1771; 1701. EI-MS m/z (rel. int.)=551 (86.49%; M$^{+•}$). $^1$H NMR (300 MHz, CDCl$_3$) 8.30 (bs; 1H; imide-NH); 7.98 (s; 1H; indole-H); 7.38 (d; $^3$J=8.1 Hz; 1H; indole-H); 7.15 (t; $^3$J=7.6 Hz; 1H; indole-H); 6.85 (t; $^3$J=7.6 Hz; 1H; indole-H); 6.80 (s; 2H; Ar—H); 6.47 (d; $^3$J=8.1 Hz; 1H; indole-H); 4.34 (t; $^3$J=6.8 Hz; 2H; indole-CH$_2$CH$_2$CH$_2$O); 3.86 (s; 3H; OCH$_3$); 3.60 (t; $^3$J=5.5 Hz; 2H indole-CH$_2$CH$_2$CH$_2$O); 3.49 (s; 6H; 2×OCH$_3$); 2.08 (m; 2H; indole-CH$_2$CH$_2$CH$_2$O); 0.94 (s; 9H; SiC(CH$_3$)$_3$); 0.07 (s; 6H; Si(CH$_3$)$_2$).

3-(1-[3-Hydroxypropyl]-1H-indol-3-yl)-4-(3,4,5-trimethoxyphenyl)-maleinimide (2.25 mmol, 75%) was synthesized using the same procedure as for example 3. Mp=160° C. IR ṽ [cm$^{-1}$]=3367; 2980; 2882; 1708. EI-MS m/z (rel. int.) =437 (100%; M$^{+•}$). $^1$H NMR (300 MHz, CDCl$_3$) 7.97 (s; 1H; indole-NH); 7.38 (m; 2H; indole-H+imide-NH); 7.17 (t; $^3$J=7.6 Hz; 1H; indole-H); 6.86 (t; $^3$J=7.6 Hz; 1H; indole-H); 6.79 (s; 2H; Ar—H); 6.49 (d; $^3$J=8.1 Hz; 1H; indole-H); 4.39 (t; $^3$J=6.79 Hz; 2H; indole-CH$_2$CH$_2$CH$_2$O); 3.86 (s; 3H; OCH$_3$); 3.65 (t; $^3$J=5.67 Hz; 2H; indole-CH$_2$CH$_2$CH$_2$O); 3.50 (s; 6H; 2×OCH$_3$); 2.13 (m, 2H; indole-CH$_2$CH$_2$CH$_2$O). Anal. calcd for C$_{24}$H$_{24}$N$_2$O$_6$: C, 66.04; H, 5.54; N, 6.42. Found: C, 65.93; H, 5.63; N, 6.34.

Example 5

3-{1-[2-(Dimethylamino)ethyl]-1H-indol-3-yl}-4-(3,4,5-trimethoxyphenyl)-maleinimide

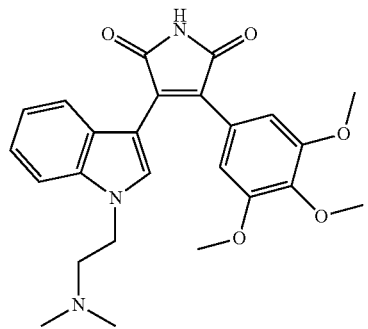 [SMILES: COc1cc(C2=C(c3cn(CCN(C)C)c4ccccc34)C(=O)NC2=O)cc(OC)c1OC]

The general procedure 1 was then followed using 1-chloro-2-dimethylaminoethane (6 mmol, 0.65 g), ethyl-2-(1H-indol-3-yl)-2-oxoacetate (6 mmol, 1.3 g) and Cs$_2$CO$_3$ (6.6 mmol, 2.15 g). The purification was achieved by column chromatography (petrolether:ethylacetate:diethylamine 6:3:1) to yield ethyl-2-{1-[2-(dimethylamino)-ethyl]-1H-indol-3-yl}-2-oxoacetate (3.7 mmol, 62%) as pale yellow crystals. Mp=71-72° C. IR ṽ [cm$^{-1}$]=3139; 3044; 2977; 2946; 2797; 2772; 1727; 1641. EI-MS m/z (rel. int.)=288 (19.15%; M$^{+•}$).

$^1$H NMR (300 MHz, CDCl$_3$) 8.45 (m; 2H; indole-H); 7.37 (m; 3H; indole-H); 4.41 (q; $^3$J=7.1 Hz; 2H; OCH$_2$CH$_3$); 4.26 (t; $^3$J=6.9 Hz; 2H; indole-CH$_2$CH$_2$N); 2.76 (t; $^3$J=6.9 Hz; 2H; indole-CH$_2$CH$_2$N); 2.31 (s; 6H); 1.44 (t; 3H; $^3$J=7.1 Hz; OCH$_2$CH$_3$).

The general procedure 2 was then followed using the above product (3.7 mmol, 1.07 g), 3,4,5-trimethoxyphenylacetamide (3.7 mmol, 0.83 g) and 1 M tert.-BuOK (10 mmol, 10 ml). The purification was achieved by column chromatography (dichloromethane:methanol 9:1) to yield 3-{1-[2-(dimethylamino)ethyl]-1H-indol-3-yl}-4-(3,4,5-trimethoxyphenyl)-maleinimide (1.34 mmol, 36%) as yellow crystals. Mp=184-185° C. IR ṽ [cm$^{-1}$]=2980; 2920; 1701. EI-MS m/z (rel. int.)=449 (100%; M$^{+•}$). $^1$H NMR (300 MHz, CDCl$_3$) 8.04 (s; 1H; indole-H); 7.97 (bs; 1H; NH); 7.34 (d; $^3$J=8.2 Hz; 1H; indole-H); 7.16 (t; $^3$J=7.6 Hz; 1H; indole-H); 6.85 (t; $^3$J=7.6 Hz; 1H; indole-H); 6.75 (s; 2H; Ar—H); 6.45 (d; $^3$J=8.2 Hz; 1H; indole-H); 4.32 (t; $^3$J=6.8 Hz; 2H indole-CH$_2$CH$_2$N); 3.84 (s; 3H; OCH$_3$); 3.47 (s; 6H; 2×OCH$_3$); 2.80 (t; $^3$J=6.8 Hz; 2H, indole-CH$_2$CH$_2$N); 2.32 (s; 6H; N(CH$_3$)$_2$). Anal. calcd for C$_{25}$H$_{27}$N$_3$O$_5$: C, 66.8; H, 6.05; N, 9.35. Found: C, 66.91; H, 6.05; N, 9.29.

Example 6

3-{1-[3-(Dimethylamino)propyl]-1H-indol-3-yl}-4-(3,4,5-trimethoxyphenyl)maleinimide

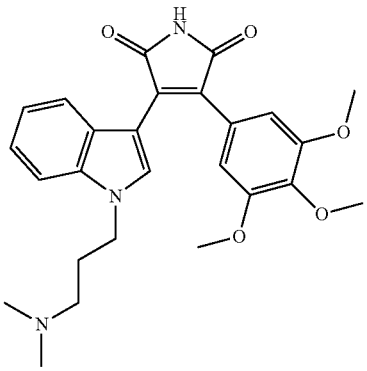

The general procedure 1 was then followed using 1-chloro-3-dimethylaminopropane (7 mmol, 0.75 g), ethyl-2-(1H-indol-3-yl)-2-oxoacetate (6 mmol, 1.3 g) and Cs$_2$CO$_3$ (6.6 mmol, 2.15 g). The purification was achieved by column chromatography (petro-lether:ethylacetate:diethylamine 6:3:1) to yield ethyl-2-{1-[2-(dimethylamino)ethyl]-1H-indol-3-yl}-2-oxoacetate (3.8 mmol, 63%) as an pale yellow oil. IR ṽ [cm$^{-1}$]=3023; 2962; 2917; 1732; 1630. EI-MS m/z (rel. int.) =302 (8.21%; M$^{+•}$). $^1$H NMR (300 MHz, CDCl$_3$) 8.43 (m; 1H; indole-H); 8.39 (s; 1H; indole-H); 7.33 (m; 3H; indole-H); 4.40 (q; $^3$J=7.1 Hz; 2H; OCH$_2$CH$_3$); 4.27 (t; $^3$J=6.8 Hz; 2H; indole-CH$_2$CH$_2$CH$_2$N); 2.22 (s; 6H; N(CH$_3$)$_2$); 2.20 (m; 2H; indole-CH$_2$CH$_2$CH$_2$N); 2.00 (quint; $^3$J=6.7 Hz; 2H; indole-CH$_2$CH$_2$CH$_2$N); 1.42 (t; $^3$J=7.1 Hz; 3H OCH$_2$CH$_3$).

The general procedure 2 was then followed using the above product (3.8 mmol, 1.15 g), 3,4,5-trimethoxyphenylacetamide (3.8 mmol, 0.83 g) and 1 M tert.-BuOK (10 mmol, 10 ml). The purification was achieved by column chromatography (dichloromethane:methanol 8:2) to yield 3-{1-[3-(dimethylamino)propyl]-1H-indol-3-yl}-4-(3,4,5-trimethoxyphenyl)-maleinimide (0.73 mmol, 19%) as orange crystals.

Mp=187-188° C. IR $\tilde{\nu}$ [cm$^{-1}$]=2939; 1705; 1613; 1578. EI-MS m/z (rel. int.)=463 (36.77%; M$^+$). $^1$H NMR (300 MHz, CDCl$_3$) 8.01 (s; 1H; indole-H); 7.78 (bs; 1H; imide-NH); 7.37 (d; $^3$J=8.1 Hz; 1H; indole-H); 7.16 (t; $^3$J=7.6 Hz; 1H; indole-H); 6.85 (t; $^3$J=7.6 Hz; 1H; indole-H); 6.79 (s; 2H; Ar—H); 6.46 (d; $^3$J=8.1 Hz; 1H; indole-H); 4.31 (t; $^3$J=6.8 Hz; 2H; indole-CH$_2$CH$_2$CH$_2$N); 3.85 (s; 3H; OCH$_3$); 3.49 (s; 6H; 2×OCH$_3$); 2.28 (m; 8H; indole-CH$_2$CH$_2$CH$_2$N+N(CH$_3$)$_2$); 2.06 (m; 2H; indole-CH$_2$CH$_2$CH$_2$N). Anal. calcd for C$_{26}$H$_{29}$N$_3$O$_5$(×⅔H$_2$O)C, 65.67; H, 6.43; N, 8.84. Found: C, 65.46; H, 6.13; N, 8.62.

Example 7

3-{1-[2-(Piperidin-1-yl)ethyl]-1H-indol-3-yl}-4-(3,4,5-trimethoxyphenyl)-maleinimide

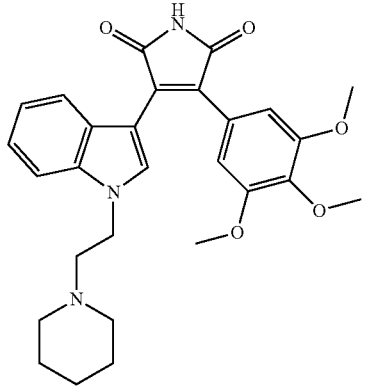 [SMILES: COc1cc(C2=C(c3cn(CCN4CCCCC4)c4ccccc34)C(=O)NC2=O)cc(OC)c1OC]

The general procedure 1 was then followed using 1-(2-chloroethyl)piperidine (10 mmol, 1.5 g), ethyl-2-(1H-indol-3-yl)-2-oxoacetate (7 mmol, 1.5 g) and K$_2$CO$_3$ (10.9 mmol, 1.5 g). The purification was achieved by column chromatography (petrol-ether:ethylacetate:diethylamine 8:1:1) to yield ethyl-2-{1-[2-(piperidin-1-yl)ethyl]-1H-indol-3-yl}2-oxoacetate (4.6 mmol, 66%) as an pale yellow oil. IR $\tilde{\nu}$ [cm$^{-1}$]=2936; 2857; 1730; 1638. EI-MS m/z (rel. int.)=328 (18.99%; M$^{+\cdot}$). $^1$H NMR (300 MHz, CDCl$_3$) 8.43 (m; 2H; indole-H); 7.35 (m; 3H; indole-H); 4.40 (q; $^3$J=7.1 Hz; 2H; OCH$_2$CH$_3$); 4.25 (t; $^3$J=6.8 Hz; 2H; indole-CH$_2$CH$_2$N); 2.72 (t; $^3$J=6.8 Hz; 2H; indole-CH$_2$CH$_2$N); 2.43 (m; 4H; piperidin-CH$_2$(C-2+6)); 1.57 (m; 4H; piperidin-CH$_2$(C-3+5)); 1.43 (m; 5H; piperidin-CH$_2$(C-4)+OCH$_2$CH$_3$).

The general procedure 2 was then followed using the above product (4.6 mmol, 1.51 g), 3,4,5-trimethoxyphenylacetamide (4.6 mmol, 1.04 g) and 1 M tert.-BuOK (14 mmol, 14 ml). The purification was achieved by column chromatography (dichloromethane:methanol 9:1) to yield 3-{1-[2-(piperidin-1-yl)ethyl]-1H-indol-3-yl}-4-(3,4,5-trimethoxyphenyl)-maleinimide (1.6 mmol, 35%) as yellow crystals. Mp=179-180° C. IR $\tilde{\nu}$ [cm$^{-1}$]=3132; 2939; 2829; 1704; 1629. EI-MS m/z (rel. int.)=491 (31.97%; M$^{+\cdot}$). $^1$H NMR (300 MHz, CDCl$_3$) 8.18 (bs; 1H; imide-NH); 8.12 (s; 1H; indole-H); 7.35 (d; $^3$J=8.1 Hz; 1H; indole-H); 7.16 (t; $^3$J=7.6 Hz; 1H; indole-H); 6.85 (t; $^3$J=7.6 Hz; 1H; indole-H); 6.77 (s; 2H; Ar—H); 6.44 (d; $^3$J=8.1 Hz; 1H; indole-H); 4.34 (t; $^3$J=7.0 Hz; 2H; indole-CH$_2$CH$_2$N); 3.85 (s; 3H; OCH$_3$); 3.48 (s; 6H; 2×OCH$_3$); 2.80 (t; $^3$J=7.0 Hz; 2H; indole-CH$_2$CH$_2$N); 2.49 (m; 4H; piperidin-CH$_2$(C-2+6)); 1.62 (m; 4H; piperidin-CH$_2$ (C-3+5)); 1.46 (m; 2H; piperidin-CH$_2$(C4)). Anal. calcd for C$_{28}$H$_{31}$N$_3$O$_5$ (×H$_2$O) C, 66.26; H, 6.55; N, 8.28. Found: C, 66.50; H, 6.57; N, 7.83.

Example 8

3-{1-(2-Morpholinoethyl)-1H-indol-3-yl}-4-(3,4,5-trimethoxyphenyl)-maleinimide

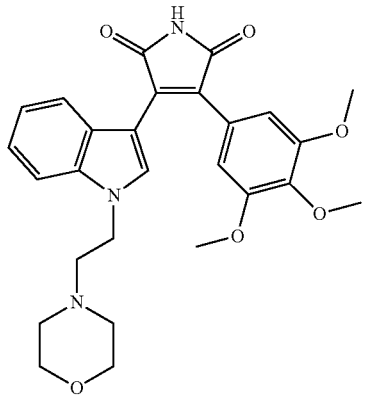 [SMILES: COc1cc(C2=C(c3cn(CCN4CCOCC4)c4ccccc34)C(=O)NC2=O)cc(OC)c1OC]

The general procedure 1 was then followed using 1-(2-chloroethyl)morpholine (10 mmol, 1.5 g), ethyl-2-(1H-indol-3-yl)-2-oxoacetate (7 mmol, 1.5 g) and K$_2$CO$_3$ (10.9 mmol, 1.5 g). The purification was achieved by column chromatography (petrolether:ethylacetate:diethylamine 5:5:1) to yield ethyl-2-[1-(2-morpholinoethyl)-1H-indol-3-yl]-2-oxoacetate (3.8 mmol, 55%) as pale yellow crystals. Mp 99-100° C. IR $\tilde{\nu}$ [cm$^{-1}$]=3164; 2955; 2822; 1717; 1625. EI-MS m/z (rel. int.)=330 (19.60%; M$^{+\cdot}$). $^1$H NMR (300 MHz, CDCl$_3$) 8.45 (m; 2H; indole-H); 7.37 (m; 3H; indole-H); 4.41 (q; $^3$J=7.1 Hz; 2H; OCH$_2$CH$_3$); 4.27 (t; $^3$J=6.5 Hz; 2H; indole-CH$_2$CH$_2$N); 3.71 (m; 4H; morpholin-CH$_2$(C3+5)); 2.79 (t; 2H; $^3$J=6.5 Hz; indole-CH$_2$CH$_2$N); 2.49 (m; 4H; morpholin-CH$_2$(C2+6)); 1.44 (t; J=7.1 Hz; 3H; OCH$_2$CH$_3$).

The general procedure 2 was then followed using the above product (3.8 mmol, 1.25 g), 3,4,5-trimethoxyphenylacetamide (3.8 mmol, 0.85 g) and 1 M tert.-BuOK (12 mmol, 12 ml). The purification was achieved by column chromatography (dichloromethane:methanol 9:1) to yield 3-{1-(2-morpholinoethyl)-1H-indol-3-yl}-4-(3,4,5-trimethoxyphenyl)-maleinimide (1 mmol, 27%) as orange crystals. Mp=238-239° C. IR $\tilde{\nu}$ [cm$^{-1}$]=3145; 2955; 1857; 1698; 1616. EI-MS m/z (rel. int.)=492 (44.94%; M$^{+\cdot}$). $^1$H NMR (300 MHz, DMSO) 11.04 (bs; 1H; imide-NH); 8.07 (s; 1H; indole-H); 7.56 (d; $^3$J=8.1 Hz; 1H; indole-H); 7.13 (t; $^3$J=7.6 Hz; 1H; indole-H); 6.78 (t; $^3$J=7.6 Hz; 1H; indole-H); 6.72 (s; 2H; Ar—H); 6.36 (d; $^3$J=8.1 Hz; 1H; indole-H); 4.40 (t; $^3$J=6.0 Hz; 2H; indole-CH$_2$CH$_2$N); 3.66 (s; 3H; OCH$_3$); 3.52 (m; 4H; morpholin-CH$_2$(C3+5)); 3.37 (s; 6H; 2×OCH$_3$); 2.68 (t; $^3$J=6.0 Hz; 2H; indole-CH$_2$CH$_2$N); 2.40 (m; 4H; morpholin- CH$_2$(C2+6)). Anal. calcd for C$_{27}$H$_{29}$N$_3$O$_6$ (x½H$_2$O)C, 64.79; H, 6.04; N, 8.39. Found: C, 64.63; H, 6.03; N, 8.23.

Example 9

3-{1-[3-(4-Methylhexahydro-1-pyrazindiylium)propyl]-1H-indol-3-yl}-4-(3,4,5-trimethoxyphenyl)-maleinimide dichloride

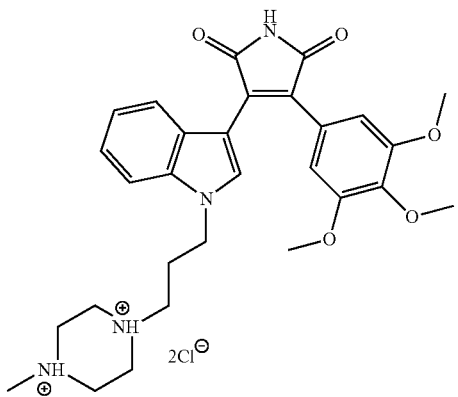

A modified procedure of Mahesh et al., *Pharmazie*, 2005, 60, 6, 411-414, was used. After cooling a stirred solution of N-methylpiperazine (50 mmol, 5.55 ml) in 100 ml acetone to 0° C., 10 ml of an aqueous 25% NaOH-solution and 1-bromo-3-chloropropane (50 mmol, 7.87 g=4.92 ml) were added cautiously. The reaction was stirred at RT for 24 hours. After concentrating the mixture under reduced pressure, the residue was diluted with water and extracted with dichloromethane. The collected organic phases were dried over Na$_2$SO$_4$, filtered and concentrated. The residue was diluted with ethanol and after adding 2.3 M ethanolic HCl 1-(3-chloropropyl)-4-methylpiperazin-dihydrochloride crystallized as white crystals (12.5 mmol, 25%). Mp=257° C. $^1$H NMR (300 MHz, DMSO) 3.74 (t; 2H; $^3$J=6.4 Hz; NCH$_2$CH$_2$CH$_2$Cl); 3.37 (m; 12H; NCH$_2$CH$_2$CH$_2$Cl+4× piperazin-CH$_2$+2×NH); 2.81 (s; 3H; CH$_3$); 2.19 (d; 2H; $^3$J=6.8 Hz; NCH$_2$CH$_2$CH$_2$Cl).

The general procedure 1 was then followed using 1-(3-chloropropyl)-4-methylpiperazine (12.5 mmol, 2.2 g), ethyl-2-(1H-indol-3-yl)-2-oxoacetate (10 mmol, 2.17 g) and K$_2$CO$_3$ (10.8 mmol, 1.5 g). The purification was achieved by column chromatography (petro-lether:ethylacetate:diethylamine 5:5:1) to yield ethyl-2-{1-[3-(4-methylpiperazin-1-yl)propyl]-1H-indol-3-yl}-2-oxoacetate (5.3 mmol, 42%). IR [cm$^{-1}$]=2936; 2790; 1727; 1638. FD-MS m/z (rel. int.) =359.9 (2.05%; M$^{+\cdot}$). $^1$H NMR (300 MHz, CDCl$_3$) 8.40 (m; 2H; indole-H); 7.36 (m; 3H; indole-H); 4.38 (q; $^3$J=7.1 Hz; 2H; OCH$_2$CH$_3$); 4.25 (t; $^3$J=6.5 Hz; 2H; indole-CH$_2$CH$_2$CH$_2$N); 2.44 (m; 8H; 4× piperazin-CH$_2$); 2.30 (s; 3H; CH$_3$); 2.26 (t; $^3$J=6.5 Hz; 2H; indole-CH$_2$CH$_2$CH$_2$N); 2.00 (m; 2H;

The general procedure 2 was then followed using the above product (5.3 mmol, 1.9 g), 3,4,5-trimethoxyphenylacetamide (5.3 mmol, 1.2 g) and 1 M tert.-BuOK (15 mmol, 15 ml). The purification was achieved by column chromatography (dichloromethane:methanol 8:2). The product was diluted with ethanol and after adding 2.3 M ethanolic HCl 3-{1-[3-(4-methylhexahydro-1-pyrazindiiumyl)propyl]-1H-indol-3-yl}-4-(3,4,5-trimethoxyphenyl)-maleinimide dichloride crystallized as orange crystals (0.93 mmol, 29%). Mp=225-226° C. IR ṽ [cm$^{-1}$]=3088; 2996; 2958; 1695. EI-MS m/z (rel. int.)=520 (27.12%; M$^{+\cdot}$). $^1$H NMR (300 MHz, DMSO) 11.11 (bs; 1H; imide-NH); 8.09 (s; 1H; indole-H); 7.64 (d; $^3$J=8.1 Hz; 1H; indole-H); 7.15 (t; $^3$J=7.6 Hz; 1H; indole-H); 6.80 (t; $^3$J=7.6 Hz; 1H; indole-H); 6.73 (s; 2H; Ar—H); 6.35 (d; $^3$J=8.1 Hz; 1H; indole-H); 4.43 (m; 2H; indole-CH$_2$CH$_2$CH$_2$N); 3.70 (m; 12H; 4× piperazin-CH$_2$+2×NH+indole-CH$_2$CH$_2$CH$_2$N); 3.65 (s; 3H; OCH$_3$); 3.37 (s; 6H; 2×OCH$_3$); 2.80 (s; 3H; CH$_3$); 2.24 (m; 2H; indole-CH$_2$CH$_2$CH$_2$N). Anal. calcd for C$_{29}$H$_{36}$Cl$_2$N$_4$O$_5$ (×2HCl×H$_2$O) C, 57.14; H, 6.28; N, 9.19. Found: C, 57.10; H, 6.30; N, 8.68.

Example 10

3-(5-Fluoro-1H-indol-3-yl)-4-(3,4,5-trimethoxyphenyl)-maleinimide

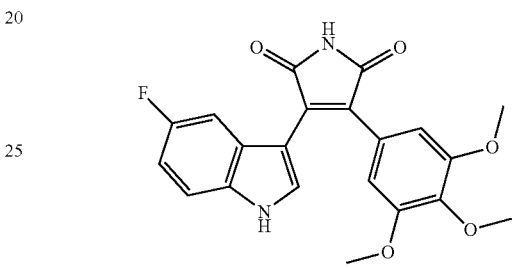

A modified procedure of Catarzi et al., *Arch. Pharm. (Weinheim)* 1997, 330, 12, 383-386, was used to prepare ethyl 2-(5-fluoro-1H-indol-3-yl)-2-oxoacetate. A stirred solution of 5-fluoroindole (7.4 mmol, 1.0 g) and pyridine (0.8 ml) in 30 ml diethylether was cooled to 0° C. Ethyloxalylchloride (8.9 mmol; 1.21 g=1.5 ml) was added cautiously over a period of 20 min. The reaction was stirred for 1 h at a temperature of 0° C. and afterwards 4 h at room temperatur. The precipitate was filtered, washed with cold diethylether and water to give ethyl 2-(5-fluor-1H-indol-3-yl)-2-oxoacetate (8 mmol; 64.8%) as pale yellow crystals. The collected organic phase was dried over Na$_2$SO$_4$, filtered, concentrated and purified by column chromatography (petroletter:ethylacetate 1:1). IR ṽ [cm$^{-1}$] =3158; 2978; 1724; 1614. EI-MS m/z (rel. Int.)=235 (9.64%; M$^{+\cdot}$). $^1$H NMR (300 MHz, CDCl$_3$) 9.22 (bs, 1H; NH); 8.53 (d; J=3.3 Hz; 1H; indole-H); 8.11 (dd; J=2.5 Hz; J=9.0 Hz; 1H; indole-H); 7.41 (dd; J=4.3 Hz; J=9.0 Hz; 1H; indole-H); 7.06 (dt; J=2.5 Hz; J=9.0 Hz; 1H; indole-H); 4.41 (q; $^3$J=7.1 Hz; 2H; OCH$_2$CH$_3$); 1.43 (t; $^3$J=7.1 Hz; 3H; OCH$_2$CH$_3$).

A modified procedure of Basel et al., *J. Org. Chem.*, 2000, 65, 20, 6368-6380, was used to prepare ethyl-2-[1-(tert:-butoxycarbonyl)-5-fluoro-1H-indol-3-yl]-2-oxoacetate. To a stirred suspension of the above ethyl 2-(5-fluoro-1H-indol-3-yl)-2-oxoacetate (4.8 mmol; 1.1 g) and di-tert.-butyldicarbonat (4.8 mmol; 1.05 g) in 30 ml dichloromethan a catalytic amounts of DMAP (dimethylaminopyridine) was added. The suspension becomes a clear solution of adding DMAP. The reaction was stirred over night, concentrated and purified by column chromatography (dichloromethane) to obtain ethyl-2-[1-(tert:-butoxycarbonyl)-5-fluoro-1H-indol-3-yl]-2-oxoacetate as white crystals (4.6 mmol; 95.8%). Mp=137-138° C. IR ṽ [cm$^{-1}$]=2974; 1753; 1736; 1663. EI-MS m/z (rel. Int.)=335 (10.61%; M$^{+\cdot}$). $^1$H NMR (300 MHz, CDCl$_3$) 8.83 (s; 1H; indole-H); 8.12 (dd; J=4.7 Hz; J=9.2 Hz; 1H; indole-H); 8.08 (dd; J=2.7 Hz; J=9.2 Hz; 1H; indole-H); 7.14

(dt; J=2.7 Hz; J=9.2 Hz; 1H; indole-H); 4.44 (q; $^3$J=7.2 Hz; 2H; OC$\underline{H}_2$CH$_3$); 1.70 (s; 9H; C(CH$_3$)$_3$); 1.45 (t; $^3$J=7.2 Hz; 3H; OCH$_2$C$\underline{H}_3$).

The general procedure 2 was then followed using the above product (4.5 mmol, 1.5 g), 3,4,5-trimethoxyphenylacetamide (4.5 mmol, 1.0 g) and 1 M tert.-BuOK (13.5 mmol, 13.5 ml). The purification was achieved by column chromatography (petrolether:ethylacetate:methanol 4.75:4.75:0.5) to yield 3-(5-fluoro-1H-indol-3-yl)-4-(3,4,5-trimethoxyphenyl)-maleinimide (1.7 mmol; 39%) as yellow crystals. Mp=232-233° C. IR $\tilde{v}$ [cm$^{-1}$]=3289; 1716; 1577. FD-MS m/z (rel. Int.) =398.1 (1.71%; M$^{+\cdot}$.). $^1$H NMR (300 MHz, DMSO) 11.99 (bs; 1H; indole-NH); 11.07 (bs; 1H; imide-NH); 8.06 (d; $^3$J=2.6 Hz; 1H; indole-H); 7.44 (dd; J=4.7 Hz; J=8.8 Hz; 1H; indole-H); 6.94 (dt; J=2.3 Hz; J=9.1 Hz; 1H; indole-H); 6.7 (s; 2H; Ar—H); 5.91 (dd; J=2.1 Hz; J=10.7 Hz; 1H, indole-H); 3.67 (s; 3H; OCH$_3$); 3.43 (s; 6H; 2×OCH$_3$). Anal. Calcd for C$_{21}$H$_{17}$FN$_2$O$_5$ C, 63.63; H, 4.32; N, 7.07. Found: C, 63.44; H, 4.45; N, 6.86.

Example 11

3-(5-Bromo-1H-indol-3-yl)-4-(3,4,5-trimethoxyphenyl)-maleinimide

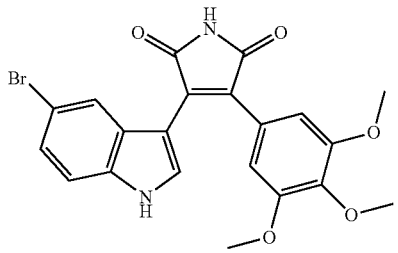 [SMILES: COc1cc(C2=C(c3c[nH]c4ccc(Br)cc34)C(=O)NC2=O)cc(OC)c1OC]

Ethyl 2-(5-brom-1H-indol-3-yl)-2-oxoacetate was prepared using the same procedure as in Example 10. The following amounts were used: 5-bromoindole (6.6 mmol; 1.29 g); ethyloxalylchloride (7.5 mmol; 1.02 g=0.83 ml); pyridine (0.7 ml); diethylether (30 ml). Ethyl 2-(5-bromo-1H-indol-3-yl)-2-oxoacetate (3.5 mmol; 53%) was obtained as pale yellow crystals. Mp=182-183° C. IR $\tilde{v}$ [cm$^{-1}$]=3224; 1720; 1618. EI-MS m/z (rel. Int.)=297 (100%; M$^{+\cdot}$.). $^1$H NMR (300 MHz, CDCl$_3$+DMSO) 11.79 (bs; 1H; NH); 8.09 (d; J=1.1 Hz; 1H; indole-H); 8.01 (d; J=3.3 Hz; 1H; indole-H); 7.01 (m; 2H; indole-H); 4.04 (q; $^3$J=7.1 Hz; 2H; OC$\underline{H}_2$CH$_3$); 1.07 (t; $^3$J=7.1 Hz; 3H; OCH$_2$C$\underline{H}_3$).

Ethyl-2-[1-(tert.-butoxycarbonyl)-5-bromo-1H-indol-3-yl]-2-oxoacetate was prepared using the same procedure as in Example 10. The following amounts were used: Ethyl 2-(5-bromo-1H-indol-3-yl)-2-oxoacetate (3.5 mmol; 1.05 g); di-tent.-butyldicarbonat (4 mmol; 0.8 g); DMAP; dichloromethan (30 ml). Ethyl-2-[1-(tert.-butoxycarbonyl)-5-bromo-1H-indol-3-yl]-2-oxoacetate was obtained as white crystals (2.6 mmol; 74.3%). Mp=159-160° C. IR $\tilde{v}$ [cm$^{-1}$] =2962; 1751; 1732; 1663 EI-MS m/z (rel. Int.)=397 (12.17%; M$^+$.). $^1$H NMR (300 MHz, CDCl$_3$) 8.78 (s; 1H; indole-H); 8.56 (d; $^5$J=2.0 Hz; 1H; indole-H); 8.05 (d, $^3$J=8.9 Hz, 1H; indole-H); 7.52 (dd; $^5$J=2.0 Hz; $^3$J=8.9 Hz; 1H; indole-H); 4.44 (q; $^3$J=7.1 Hz; 2H; OC$\underline{H}_2$CH$_3$); 1.70 (s; 9H; C(CH$_3$)$_3$); 1.45 (t; $^3$J=7.1 Hz; 3H; OCH$_2$C$\underline{H}_3$).

The general procedure 2 was then followed using the above product (2.6 mmol, 1.02 g), 3,4,5-trimethoxyphenylacetamide (2.7 mmol, 0.6 g) and 1 M tert.-BuOK (8 mmol, 8 ml). The purification was achieved by column chromatography (petrolether:ethylacetat:methanol 4.5:4.5:1) to yield 3-(5-bromo-1H-indol-3-yl)-4-(3,4,5-trimethoxyphenyl)-maleinimide (0.68 mmol; 26%) as orange crystals. Mp=259-262° C. IR $\tilde{v}$ [cm$^{-1}$]=3342; 1708; 1614. FD-MS m/z (rel. Int.)=458.1 (38.24%; M$^{+\cdot}$.). $^1$H NMR (300 MHz, DMSO) 12.07 (bs; 1H; indole-NH); 11.08 (bs; 1H; imide-NH); 8.05 (d; $^3$J=2.7 Hz; 1H; indole-H); 7.40 (d; $^3$J=8.6 Hz; 1H; indole-H); 7.20 (dd; $^5$J=1.6 Hz; $^3$J=8.6 Hz; 1H; indole-H); 6.68 (s; 2H; Ar—H); 6.38 (s; 1H; indole-H); 3.71 (s; 3H; OCH$_3$); 3.43 (s; 6H; 2×OCH$_3$). Anal. Calcd for C$_{21}$H$_{17}$BrN$_2$O$_5$ C, 55.16; H, 3.75; N, 6.13. Found: C, 55.06; H, 3.87; N, 6.01.

Example 12

3-(4-Azaindol-3-yl)-4-(3,4,5-trimethoxyphenyl)-1H-pyrrol-2,5-dione

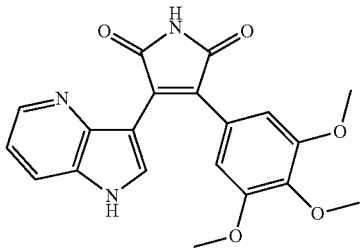 [SMILES: COc1cc(C2=C(c3c[nH]c4cccnc34)C(=O)NC2=O)cc(OC)c1OC]

(a) Dimethyl-2-(3-nitropyridin-2-yl)malonate

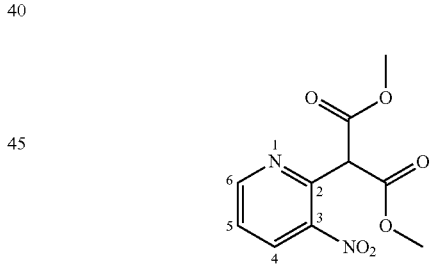

A modified procedure of Cash et al. (Org. Biomol. Chem. 2005, 3, 3701-3706) was used. 2-Chloro-3-nitropyridine (2 g, 12.5 mmol) was added to a stirred suspension of NaH (0.5 g, 12.5 mmol; mixture of 60% NaH mineral oil) in 20 ml dry DMF under nitrogen. Dimethylmalonate (1.43 ml, 1.65 g, 12.5 mmol) was cautiously added dropwise. After the reaction was stirred for 5 h at room temperature, the solution was diluted with water. After adding diethylether the mixture was washed with saturated NaCl solution for four times to remove the DMF. The organic phase was dried over Na$_2$SO$_4$, filtered, concentrated and purified by column chromatography (petrolether:ethylacetate 2:1). Dimethyl-2-(3-nitropyridin-2-yl) malonate was obtained as a pale brown oil (1.4 g, 5.5 mmol=44%). $^1$H NMR (300 MHz, CDCl$_3$) 8.83 (pdd; $^3$J=1.3 Hz; $^3$J=4.7 Hz; 1H; H-6); 8.49 (pdd; $^3$J=1.3 Hz; $^3$J=8.3 Hz;

1H; H-4); 7.54 (pdd; $^3J$=4.7 Hz; $^3J$=8.3 Hz; 1H; H-5); 5.56 (s; 1H; CH); 3.83 (s; 6H; OCH$_3$).

(b) 2-Methyl-3-nitropyridine

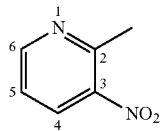

A modified procedure of Cash et al. (Org. Biomol. Chem. 2005, 3. 3701-3706) was used. Dimethyl-2-(3-nitropyridin-2-yl)malonate (1.4 g, 5.5 mmol) was dissolved in 70 ml 6 M HCl and refluxed for 8 h. After neutralization with saturated Na$_2$CO$_3$ solution the solution was extracted three times with dichloromethane. The combined organic layers were dried over Na$_2$SO$_4$, filtered, concentrated and purified by bulb tube distillation (0.35 mbar; 70-80° C.). 2-Methyl-3-nitropyridine (0.7 g, 5.1 mmol, 92%) was obtained as a pale yellow oil. $^1$H NMR (300 MHz, CDCl$_3$) 8.72 (pdd; $^3J$=1.2 Hz; $^3J$=4.7 Hz; 1H; H-6); 8.27 (pdd; $^3J$=1.2 Hz; $^3J$=8.2 Hz; 1H; H-4); 7.35 (pdd; $^3J$=4.7 Hz; $^3J$=8.2 Hz; 1H; H-5); 2.86 (s; 3H; CH$_3$).

(c) (E)-N,N-Dimethyl-2-(3-nitropyridin-2-yl)ethenamine

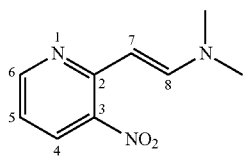

A modified procedure of Cash et al. (Org. Biomol. Chem. 2005, 3. 3701-3706) was used. 2-Methyl-3-nitropyridine (0.7 g, 5.1 mmol) was dissolved in 15 ml dry DMF and stirred under nitrogen. Dimethylformamiddimethylacetal (DMF-DMA) (1.35 ml, 1.22 g, 10.2 mmol) was added dropwise. The reaction was heated to 90° C. for 4 h. After approximately 15 min a deep redish color appeared. After evaporating the solvent (E)-N,N-Dimethyl-2-(3-nitropyridin-2-yl)ethenamine is obtained as a red oil (0.16 g, 0.8 mmol, 73%) which can be used without further purification. $^1$H NMR (300 MHz, CDCl$_3$) 8.40 (pdd; $^3J$=1.7 Hz; $^3J$=4.4 Hz; 1H; H-6); 8.16 (pdd; $^3J$=1.7 Hz; $^3J$=8.3 Hz; 1H; H-4); 8.04 (d; $^3J_{AX}$=12.5 Hz; 1H; H-8); 6.76 (pdd; $^3J$=4.4 Hz; $^3J$=8.3 Hz; 1H; H-5); 6.15 (d; $^3J_{AX}$=12.5 Hz; 1H; H-7); 3.01 (s; 6H; CH$_3$).

(d) 4-Azaindole

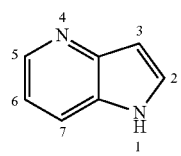

A modified procedure of Cash et al. (Org. Biomol. Chem. 2005, 3. 3701-3706) was used. 0.2 g of 10% Pd/C was flashed with nitrogen before 10 ml of a mixture of 8.8% formic acid in methanol was added cautiously. The crude (E)-N,N-Dimethyl-2-(3-nitropyridin-2-yl)ethenamine obtained as a red oil (0.69 g, 3.6 mmol) was also dissolved in 10 ml of a mixture of 8.8% formic acid in methanol before it was added to the reaction. The reaction was stirred for 4 h until the red color completely disappeared. The Pd catalyst was removed by filtration through Celite®, the filtrate was concentrated. After sitting over night, the product, 4-azaindole, crystallized (0.21 g, 1.8 mmol, 71%). $^1$H NMR (300 MHz, CDCl$_3$) 9.00 (bs; 1H; NH); 8.48 (pdd; $^4J$=1 Hz; $^3J$=4.6 Hz; 1H; H-5); 7.70 (pdd; $^4J$=1 Hz; $^3J$=8.2 Hz; 1H; H-7); 7.48 (pt; $^3J$=2.9 Hz; 1H; H-2); 7.12 (pdd; $^3J$=4.6 Hz; $^3J$=8.2 Hz; 1H; H-6); 6.76 (m; 1H; H-3).

(e) Ethyl-2-(4-azaindol-3-yl)-2-oxoacetate

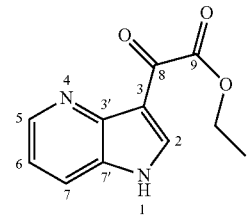

Aluminium chloride (3.1 g, 23 mmol) and 4-azaindole (0.38 g, 4.6 mmol) were stirred in 100 ml dry dichloromethane at room temperature under nitrogen atmosphere. After 30 min ethoxalylchloride (2.5 ml, 3.0 g, 23 mmol) was added dropwise. The reaction mixture was stirred over night and then carefully hydrolyzed with ethanol/ice. After addition of dichloromethane the organic layer was separated, washed with NaHCO$_3$ solution, dried over Na$_2$SO$_4$, filtered and concentrated. After sitting over night ethyl-2-(4-azaindol-3-yl)-2-oxoacetate (0.5 g, 2.3 mmol, 50%) crystallized as a pale yellow powder. $^1$H NMR (300 MHz, CDCl$_3$) 12.21 (bs; 1H; NH); 8.58 (s; 1H; H-2); 8.49 (pdd; $^3J$=4.6 Hz; $^4J$=1.3 Hz; 1H; H-5); 7.93 (pdd; $^3J$=8.2 Hz; $^4J$=1.3 Hz; 1H; H-7); 7.27 (pdd; $^3J$=8.2 Hz; $^3J$=4.6 Hz; 1H; H-6); 4.37 (q; $^3J$=7.1 Hz; 2H; CH$_2$); 1.31 (t; $^3J$=7.1 Hz; 3H; CH$_3$).

(f) Ethyl-2-[1-(tert.-butoxycarbonyl)-4-azaindol-3-yl]-2-oxoacetate

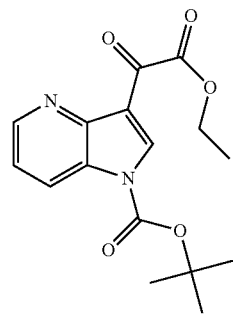 [SMILES: CCOC(=O)C(=O)c1cn(C(=O)OC(C)(C)C)c2cccnc12]

Di-tert.-butyldicarbonate (0.48 g, 2.2 mmol) and a catalytic amount of DMAP were added to a stirred solution of ethyl-2-(4-azaindol-3-yl)-2-oxoacetate (0.48 g, 2.2 mmol) in 10 ml dichloromethane. After 2 h the solvent was evaporated and the residue was purified by column chromatography to yield ethyl-2-[1-(tert.-butoxycarbonyl)-4-azaindol-3-yl]-2-oxoacetate (0.6 g, 1.9 mmol, 86%) as pale yellow crystals. $^1$H NMR (300 MHz, CDCl$_3$) 8.86 (s; 1H; H-2); 8.72 (pdd; $^4$J=1.4 Hz; $^3$J=4.7 Hz; 1H; H-5); 8.42 (pdd; $^4$J=1.4 Hz; $^3$J=8.4 Hz; 1H; H-7); 7.32 (pdd; $^3$J=4.7 Hz; $^3$J=8.4 Hz; 1H; H-6); 4.45 (q; J=7.1 Hz; 2H; CH$_2$); 1.70 (s; 9H; C(CH$_3$)$_3$); 1.43 (t; $^3$J=7.1 Hz; 3H; CH$_3$).

(g) 3-(4-Azaindol-3-yl)-4-(3,4,5-trimethoxyphenyl)-1H-pyrrol-2,5-dione

A stirred solution of 3,4,5-trimethoxyphenylacetamide (0.38 g, 1.7 mmol) and ethyl-2-[1-(tert.-butoxycarbonyl)-4-azaindol-3-yl]-2-oxoacetate (0.54 g, 1.7 mmol) in dry THF (tetrahydrofurane) containing 15 g molecular sieve (4 Å) was cooled to 0° C. under nitrogen. At this temperature 1.0 M tert.-BuOK (3.7 ml, 3.62 mmol) was added via septum and the mixture was allowed to warm to room temperature. After stirring over night, the reaction was again cooled to 0° C. and quenched with saturated NH$_4$Cl-solution. The residue was filtered, extracted with ethylacetate and the combined organic layers were dried over Na$_2$SO$_4$, concentrated and purified by column chromatography (ethylacetate:ethanol 9:1). 3-(4-azaindolyl)-4-(3,4,5-trimethoxyphenyl)-maleinimide was obtained as yellow crystals (0.17 g, 0.45 mmol, 26%). Mp=274-275° C. IR $\tilde{\nu}$ [cm$^{-1}$]=3338; 2946; 1716. EI-MS m/z (rel. int.)=380.75 (1.37%; M$^{+\cdot}$.); 379.79 (25.54%); 378.79 (71.14%); NMR (300 MHz, DMSO) 11.98 (bs; 1H; azaindole-NH); 11.14 (bs; 1H; imide-NH); 8.12 (pdd; $^4$J=1.0 Hz; $^3$J=4.6 Hz; 1H; H-5); 8.04 (pd; $^3$J=2.7 Hz; 1H; H-2); 7.83 (pdd; $^4$J=1.0 Hz; $^3$J=8.2 Hz; 1H; H-7); 7.09 (pdd; $^3$J=4.6 Hz; $^3$J=8.2 Hz; 1H; H-6); 6.87 (s; 2H; Ar—H); 3.62 (s; 3H; OCH$_3$); 3.32 (s; 6H; OCH$_3$).

The invention claimed is:
1. 3-(Indolyl)- and 3-(azaindolyl)-4-phenylmaleimide compounds of formula I

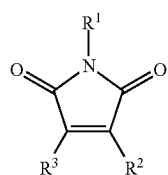

wherein
$R^1$ is H, $C_1$-$C_6$-alkyl, phenyl-$C_1$-$C_4$-alkyl or phenyl;
$R^2$ is a group having the formula

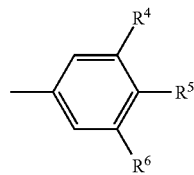

wherein $R^4$, $R^5$ and $R^6$ are $C_1$-$C_6$-alkoxy;
$R^3$ is selected from the group consisting of:

a) 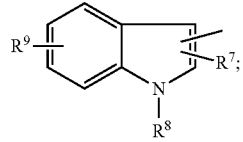

b) 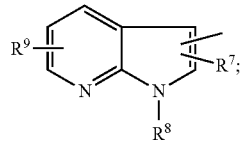

c) 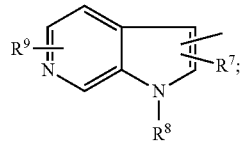

d) 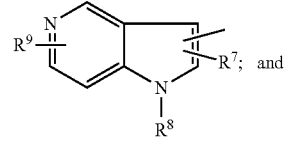

e) 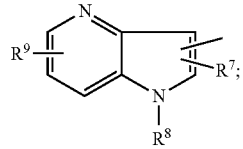

wherein $R^7$ is H or $C_1$-$C_6$-alkyl,
$R^8$ is $C_1$-$C_6$-alkyl-$R^{10}$ and $R^{10}$ is selected from the group consisting of:
a) amino,
b) $C_1$-$C_6$-alkylamino,
c) di-$C_1$-$C_6$-alkylamino,
d) hydroxy,
e) $C_1$-$C_6$-alkoxy,
f) saturated heterocyclyl with 5 or 6 ring atoms containing a nitrogen heteroatom and optionally 1 or 2 additional heteroatoms which are independently selected from O, N and S, wherein the heterocyclyl is attached to the $C_1$-$C_6$-alkyl group via the nitrogen atom and may carry an additional $C_1$-$C_6$-alkyl substituent at a carbon atom or a nitrogen atom;
g) phenoxy,
h) benzyloxy,
i) $R^{11}$CONR$^{12}$—,
j) NR$^{12}$R$^{12}$CO—,
k) $C_1$-$C_6$-alkyl-NHCONH—,
l) $C_1$-$C_6$-alkyl-NHCOO—,
m) $C_1$-$C_6$-alkyl-OCONH—,
n) $R^{12}$—OSO$_2$O—,
o) $R^{11}$SO$_2$O—,
p) $R^{12}$—OSO$_2$—,
q) $R^{11}$SO$_2$—,
r) ($R^{12}$O)$_2$P(O)O—, s) $(R^{12}O)_2P(O)$—, and t) $(R^{12}O)R_{11}P(O)O$—;

$R^9$ is H, $C_1$-$C_6$-alkyl, $C_1$-$C_6$-alkoxy, OH, or halogen;

$R^{11}$ is $C_1$-$C_6$-alkyl;

$R^{12}$ is $C_1$-$C_6$-alkyl;

and the physiologically acceptable salts thereof as well as the solvates of the compounds of formula I and of the salts thereof.

2. The compounds of claim 1

(1) having formula Ia:

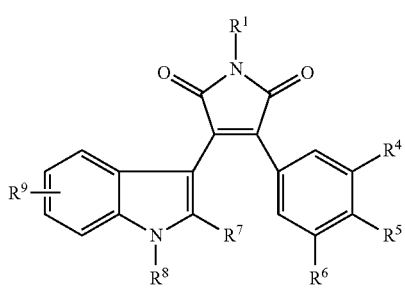
(Ia)

wherein $R^1$ and $R^7$ to $R^9$ are as defined in claim 1 and $R^4$, $R^5$ and $R^6$ are $C_1$-$C_6$-alkoxy;

(2) having formula Ib:

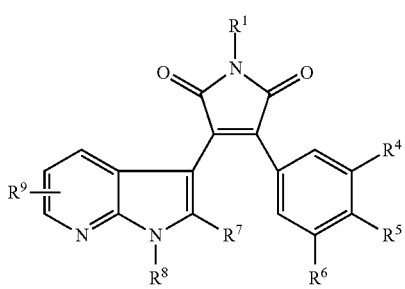
(Ib)

wherein $R^1$ and $R^7$ to $R^9$ are as defined in claim 1 and $R^4$, $R^5$ and $R^6$ are $C_1$-$C_6$-alkoxy;

(3) having formula Ic:

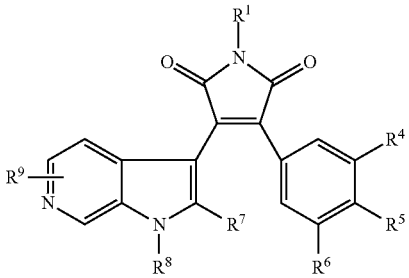
(Ic)

wherein $R^1$ and $R^7$ to $R^9$ are as defined in claim 1 and $R^4$, $R^5$ and $R^6$ are $C_1$-$C_6$-alkoxy;

(4) having formula Id:

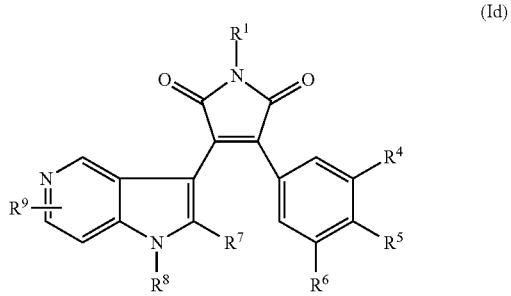
(Id)

wherein $R^1$ and $R^7$ to $R^9$ are as defined in claim 1 and $R^4$, $R^5$ and $R^6$ are $C_1$-$C_6$-alkoxy;

(5) having formula Ie:

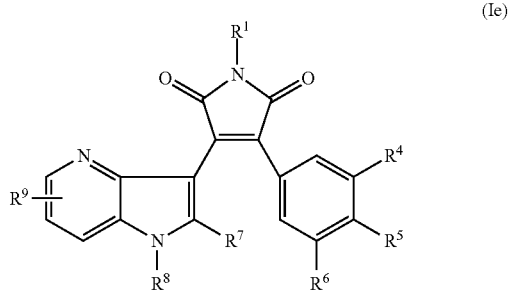
(Ie)

wherein $R^1$ and $R^7$ to $R^9$ are as defined in claim 1 and $R^4$, $R^5$ and $R^6$ are $C_1$-$C_6$-alkoxy.

3. The compounds of claim 1, wherein $R^1$, $R^7$ and $R^9$ are H.

4. The compounds of claim 1, wherein $R^{10}$ is selected from the group consisting of:

a) amino, b) $C_1$-$C_6$-alkylamino, c) di-$C_1$-$C_6$-alkylamino, d) hydroxy, e) $C_1$-$C_6$-alkoxy, and f) saturated heterocyclyl with 5 or 6 ring atoms containing a nitrogen heteroatom and optionally 1 or 2 additional heteroatoms which are independently selected from O, N and S, wherein the heterocyclyl is attached to the $C_1$-$C_6$-alkyl group via the nitrogen atom and may carry an additional $C_1$-$C_6$-alkyl substituent at a carbon atom or a nitrogen atom.

5. A pharmaceutical composition comprising at least one compound of formula I according to claim 1 and a pharmaceutically acceptable excipient.

6. The composition of claim 5, wherein the composition further comprises a chemotherapeutic agent.

7. The composition of claim 6, wherein the chemotherapeutic agent is a topoisomerase I inhibitor.

8. The composition of claim 6, wherein the chemotherapeutic agent is selected from antineoplastic agents, multidrug resistance reversing agents; and biological response modifiers, and combinations thereof.

9. The composition of claim 7, wherein the topoisomerase I inhibitor is selected from irinotecan, topotecan, rubitecan, exatecan, lurtotecan, gimatecan, prothecan, karenitecin, belotecan, silatecan and diflomotecan and the salts thereof.

10. The composition of claim 7, wherein the topoisomerase I inhibitor is irinotecan or topotecan.

* * * * *